US012755377B2

(12) United States Patent
Kudo

(10) Patent No.: US 12,755,377 B2
(45) Date of Patent: Oct. 6, 2026

(54) METHOD OF GENERATING TRAINED MODEL, MACHINE LEARNING SYSTEM, PROGRAM, AND MEDICAL IMAGE PROCESSING APPARATUS

(71) Applicant: FUJIFILM Corporation, Tokyo (JP)

(72) Inventor: Akira Kudo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 397 days.

(21) Appl. No.: 18/357,991

(22) Filed: Jul. 24, 2023

(65) Prior Publication Data

US 2024/0005498 A1 Jan. 4, 2024

Related U.S. Application Data

(63) Continuation of application No. PCT/JP2022/002132, filed on Jan. 21, 2022.

(30) Foreign Application Priority Data

Jan. 27, 2021 (JP) ................................ 2021-010914

(51) Int. Cl.

*G06K 9/00* (2022.01)
*G06T 7/00* (2017.01)
(Continued)

(52) U.S. Cl.

CPC ............ *G06T 7/0012* (2013.01); *G06V 10/82* (2022.01); *G16H 30/40* (2018.01);
(Continued)

(58) Field of Classification Search

None
See application file for complete search history.

(56) References Cited

U.S. PATENT DOCUMENTS

| | | | |
|---|---|---|---|
| 11,580,642 | B2 | 2/2023 | Akahori |
| 2019/0261945 | A1 | 8/2019 | Funka-Lea et al. |

(Continued)

FOREIGN PATENT DOCUMENTS

| | | |
|---|---|---|
| JP | 2019149094 | 9/2019 |
| JP | 2020054579 | 4/2020 |
| JP | 2020196102 | 12/2020 |

OTHER PUBLICATIONS

Cheng-Bin Jin et al., "Deep CT to MR Synthesis Using Paired and Unpaired Data", sensors, May 22, 2019, pp. 1-19, vol. 19, No. 2361.

(Continued)

*Primary Examiner* — Wei Wen Yang
(74) *Attorney, Agent, or Firm* — JCIPRNET

(57) ABSTRACT

By using a learning model having a structure of a generative adversarial network including a first generator configured using a first convolutional neural network that receives an input of a medical image of a first domain and that outputs a first generated image of a second domain, and a first discriminator configured using a second convolutional neural network that receives an input of data including first image data, which is the first generated image or a medical image of the second domain included in a training dataset and coordinate information of a human body coordinate system corresponding to each position of a plurality of unit elements configuring the first image data, and that discriminates authenticity of the input image, a computer acquires a plurality of pieces of training data including the medical image of the first domain and the medical image of the second domain; and performs training processing.

13 Claims, 15 Drawing Sheets

(51) Int. Cl.
*G06V 10/82* (2022.01)
*G16H 30/40* (2018.01)

(52) U.S. Cl.
CPC ............... *G06T 2207/10072* (2013.01); *G06T 2207/20048* (2013.01); *G06T 2207/20081* (2013.01); *G06T 2207/20084* (2013.01); *G06V 2201/031* (2022.01)

(56) References Cited

U.S. PATENT DOCUMENTS

| | | | | |
|---|---|---|---|---|
| 2019/0378274 | A1 | 12/2019 | Garnavi et al. | |
| 2021/0244971 | A1* | 8/2021 | Hibbard | G06T 7/0012 |
| 2022/0318956 | A1* | 10/2022 | Xu | G06T 5/50 |

OTHER PUBLICATIONS

Rosanne Liu et al., "An intriguing failing of convolutional neural networks and the CoordConv solution", retrieved from arXiv database, arXiv:1807.03247v2 [cs.CV], Dec. 3, 2018, pp. 1-26.

Jun-Yan Zhu et al., "Unpaired Image-to-Image Translation using Cycle-Consistent Adversarial Networks", retrieved from arXiv database, arXiv:1703.10593v7 [cs.CV], Aug. 24, 2020, pp. 1-18.

Chieh Hubert Lin et al., "COCO-GAN: Generation by Parts via Conditional Coordinating", retrieved from arXiv database, arXiv:1904.00284v4 [cs.LG], Jan. 5, 2020, pp. 1-25.

"International Search Report (Form PCT/ISA/210) of PCT/JP2022/002132", mailed on Mar. 29, 2022, with English translation thereof, pp. 1-6.

"Written Opinion of the International Searching Authority (Form PCT/ISA/237) of PCT/JP2022/002132", mailed on Mar. 29, 2022, with English translation thereof, pp. 1-6.

"Search Report of Europe Counterpart Application", issued on Jul. 9, 2024, p. 1-p. 5.

Yang Lei et al., "Generative Adversarial Network for Image Synthesis", arXiv:2012.15446v1 [physics.med-ph], Dec. 2020, pp. 1-20.

Zizhao Zhang et al., "Translating and Segmenting Multimodal Medical vols. with Cycle- and Shape-Consistency Generative Adversarial Network", 2018 IEEE/CVF Conference on Computer Vision and Pattern Recognition, Jun. 2018, pp. 9242-9251.

"Notice of Reasons for Refusal of Japan Counterpart Application", issued on Oct. 16, 2025, with English translation thereof, p. 1-p. 8.

* cited by examiner syn-MR

CT

METHOD OF GENERATING TRAINED MODEL, MACHINE LEARNING SYSTEM, PROGRAM, AND MEDICAL IMAGE PROCESSING APPARATUS

CROSS-REFERENCE TO RELATED APPLICATIONS

The present application is a Continuation of PCT International Application No. PCT/JP2022/002132 filed on Jan. 22, 2022 claiming priority under 35 U.S.C § 119(a) to Japanese Patent Application No. 2021-010914 filed on Jan. 27, 2021. Each of the above applications is hereby expressly incorporated by reference, in its entirety, into the present application.

BACKGROUND OF THE INVENTION

1. Field of the Invention

The present invention relates to a method of generating a trained model, a machine learning system, a program, and a medical image processing apparatus, and more particularly, to a machine learning technology and an image processing technology that handle medical images.

2. Description of the Related Art

In the medical field, image diagnosis is performed using a medical image captured by various modalities such as a computed tomography (CT) apparatus or a magnetic resonance imaging (MRI) apparatus. In recent years, development of artificial intelligence (AI) for performing extraction of a part such as an organ, detection of a lesion region, classification of a disease name, or the like from a medical image using deep learning has been in progress.

In JP2019-149094A, a diagnosis support system that extracts an organ region from a medical image using AI is described. In JP2020-54579A, a machine learning method of obtaining a learning model for generating a magnetic resonance (MR) estimation image obtained by estimating an MR image from a CT image is described.

In Cheng-Bin Jin, Hakil Kim, Mingjie Liu, Wonmo Jung, Seongu Joo, Eunsik Park, Young Saem Ahn, In Ho Han, Jae Il Lee, Xuenan Cui, "Deep CT to MR Synthesis Using Paired and Unpaired Data", Sensors 2019. 19(10), 23611, a method of generating a T2 weighted image of MRI from a CT image using machine learning is described. In Rosanne Liu, Joel Lehman, Piero Molino, Felipe Petroski Such, Eric Frank, Alex Sergeev, Jason Yosinski, "An intriguing failing of convolutional neural networks and the CoordConv solution", ArXiv: 1807.03247, a method of adding a channel representing coordinate information of each pixel in an image and incorporating position information into a convolutional neural network is proposed.

In Jun-Yan Zhu, Taesung Park, Phillip Isola, Alexei A. Efros, "Unpaired Image-to-Image Translation using Cycle-Consistent Adversarial Networks", ArXiv: 1703.10593, a technology capable of training mutual conversion between heterogeneous domain images using a dataset for each domain without using a pair of images as training data by using a network obtained by combining two configurations of generative adversarial networks (GAN) is disclosed.

SUMMARY OF THE INVENTION

Medical images are generated by various modalities, and features of the images are different for each modality. A computer aided diagnosis (computer aided diagnosis, computer aided detection: CAD) system or the like using AI is generally constructed for each modality that captures a target medical image. In a case where a technology constructed by a specific modality can be applied to images of other modalities, utilization in more scenes is expected.

For example, in a case where an organ extraction CAD system that receives a CT image as input and extracts a region of an organ is constructed, based on this technology, applications such as implementing the extraction of a region of an organ from a magnetic resonance (MR) image are also possible.

For this purpose, for example, a high-performance image converter that performs image conversion between heterogeneous modalities, such as processing of generating a pseudo MR image from a CT image, or conversely, processing of generating a pseudo CT image from an MR image, is required. The "image conversion" may be rephrased as "image generation", and the converter may be rephrased as "generator".

In a case of training such an image conversion task of heterogeneous modality by a deep learning-based algorithm, CycleGAN described in Jun-Yan Zhu, Taesung Park, Phillip Isola, Alexei A. Efros, "Unpaired Image-to-Image Translation using Cycle-Consistent Adversarial Networks", ArXiv: 1703.10593 is exemplified as a typical method. In CycleGAN, each dataset belonging to two domains is prepared, and mutual conversion of the domains is trained. The feature of the generated image generated by the learning model depends on the data used for training. Therefore, for example, in a case of training a CycleGAN learning model using a dataset belonging to the CT domain and a dataset belonging to the MR domain, it is assumed that these datasets are obtained by imaging the same portion region. In a case where the misregistration between the datasets is large, a region that can be observed only with data of one domain is present. In a case where training is performed using data with a large misregistration as described above, the images of different domains do not correspond to each other and training is not appropriately performed.

The technology described in Cheng-Bin Jin, Hakil Kim, Mingjie Liu, Wonmo Jung, Seongu Joo, Eunsik Park, Young Saem Ahn, In Ho Han, Jae Il Lee, Xuenan Cui, "Deep CT to MR Synthesis Using Paired and Unpaired Data", Sensors 2019.19(10), 2361 is sensitive to the misregistration between datasets, and in a case where data with the large misregistration is used for training, a generated image may fail.

The above-described problems are not limited to CycleGAN, and are perceived as a problem common to training of the image conversion task using the algorithm of GAN.

The present disclosure is conceived in view of such circumstances, and an object of the present disclosure is to provide a method of generating a trained model, a machine learning system, a program, and a medical image processing apparatus that can implement conversion training robust against a misregistration between datasets used for training.

A method of generating a trained model according to an aspect of the present disclosure, the trained model converting a domain of a medical image which is input, and outputting a generated image of a different domain, in which a learning model is used, which has a structure of a generative adversarial network including a first generator configured using a first convolutional neural network that receives an input of a medical image of a first domain and that outputs a first generated image of a second domain different from the first domain, and a first discriminator configured using a second convolutional neural network that receives an input of data including first image data, which is the first generated image generated by the first generator or a medical image of the second domain included in a training dataset, and coordinate information of a human body coordinate system corresponding to each position of a plurality of unit elements configuring the first image data, and that discriminates authenticity of the input image, and the method comprises: by a computer, acquiring a plurality of pieces of training data including the medical image of the first domain and the medical image of the second domain; and performing training processing of training the first generator and the first discriminator in an adversarial manner based on the plurality of pieces of training data.

According to the present aspect, the coordinate information of the human body coordinate system is introduced into the medical image used for training, and the data including the first image data which is a target image of the authenticity discrimination and the coordinate information corresponding to each of the plurality of unit elements in the first image data is given as the input to the first discriminator. The first discriminator performs convolution on the data to learn the authenticity according to a position indicated by the coordinate information. According to the present aspect, the robustness against the misregistration of the data used for the training is improved, and the training of the appropriate image conversion (image generation) can be implemented. The unit element of the three-dimensional image may be understood as a voxel, and the unit element of the two-dimensional image may be understood as a pixel.

In the method of generating a trained model according to another aspect of the present disclosure, the coordinate information corresponding to the first generated image in a case where the first generated image is input to the first discriminator may be coordinate information determined for the medical image of the first domain which is a conversion source image input to the first generator in a case of generating the first generated image.

In the method of generating a trained model according to still another aspect of the present disclosure, the first image data may be three-dimensional data, the coordinate information may include x coordinate information, y coordinate information, and z coordinate information that specify a position of each voxel as the unit element in a three-dimensional space, and the x coordinate information, the y coordinate information, and the z coordinate information may be used as channels and may be combined with a channel of the first image data or a feature map of the first image data to be given to the first discriminator.

In the method of generating a trained model according to still yet another aspect of the present disclosure, the coordinate information of the human body coordinate system may be an absolute coordinate defined with reference to an anatomical position of a portion of a human body, and for each medical image used as the training data, the coordinate information corresponding to each unit element in the image may be associated.

In the method of generating a trained model according to still yet another aspect of the present disclosure, the method may further comprise, by the computer, generating, for each medical image used as the training data, the coordinate information corresponding to each unit element in the image.

In the method of generating a trained model according to still yet another aspect of the present disclosure, coordinate information may be input in an interlayer of the second convolutional neural network.

In the method of generating a trained model according to still yet another aspect of the present disclosure, the learning model may further include a second generator configured using a third convolutional neural network that receives an input of the medical image of the second domain and that outputs a second generated image of the first domain, and a second discriminator configured using a fourth convolutional neural network that receives an input of data including second image data, which is the second generated image generated by the second generator or the medical image of the first domain included in the training dataset, and coordinate information of the human body coordinate system corresponding to each position of a plurality of unit elements configuring the second image data, and that discriminates the authenticity of the input image, and the training processing may include processing of training the second generator and the second discriminator in an adversarial manner.

In the method of generating a trained model according to still yet another aspect of the present disclosure, the coordinate information corresponding to the second generated image in a case where the second generated image is input to the second discriminator may be coordinate information determined for the medical image of the second domain which is a conversion source image input to the second generator in a case of generating the second generated image.

In the method of generating a trained model according to still yet another aspect of the present disclosure, the method may further comprise: by the computer, performing processing of calculating a first reconstruction loss of conversion processing using the first generator and the second generator in this order based on a first reconstructed generated image output from the second generator by inputting the first generated image of the second domain output from the first generator to the second generator, and processing of calculating a second reconstruction loss of conversion processing using the second generator and the first generator in this order based on a second reconstructed generated image output from the first generator by inputting the second generated image of the first domain output from the second generator to the first generator.

In the method of generating a trained model according to still yet another aspect of the present disclosure, the medical image of the first domain may be a first modality image captured using a first modality which is a medical apparatus, the medical image of the second domain may be a second modality image captured using a second modality which is a medical apparatus of a different type from the first modality, and the learning model may receive an input of the first modality image and may be trained to generate a pseudo second modality generated image having a feature of the image captured using the second modality.

A machine learning system for training a learning model according to still yet another aspect of the present disclosure, the learning model converting a domain of a medical image which is input and generating a generated image of a different domain, the system comprises at least one first processor, and at least one first storage device in which a program executed by the at least one first processor is stored, in which the learning model has a structure of a generative adversarial network including a first generator configured using a first convolutional neural network that receives an input of a medical image of a first domain and that outputs a first generated image of a second domain different from the first domain, and a first discriminator configured using a second convolutional neural network that receives an input of data including first image data, which is the first generated image generated by the first generator or a medical image of the second domain included in a training dataset, and coordinate information of a human body coordinate system corresponding to each position of a plurality of unit elements configuring the first image data, and that discriminates authenticity of the input image, and the at least one first processor, by executing an instruction of the program, acquires a plurality of pieces of training data including the medical image of the first domain and the medical image of the second domain, and performs training processing of training the first generator and the first discriminator in an adversarial manner based on the plurality of pieces of training data.

A program according to still yet another aspect of the present disclosure is a program that causes a computer to execute processing of training a learning model that converts a domain of a medical image which is input, and generates a generated image of a different domain, in which the learning model having a structure of a generative adversarial network including a first generator configured using a first convolutional neural network that receives an input of a medical image of a first domain and that outputs a first generated image of a second domain different from the first domain, and a first discriminator configured using a second convolutional neural network that receives an input of data including first image data, which is the first generated image generated by the first generator or a medical image of the second domain included in a training dataset, and coordinate information of a human body coordinate system corresponding to each position of a plurality of unit elements configuring the first image data, and that discriminates authenticity of the input image, and the program causes the computer to execute: acquiring a plurality of pieces of training data including the medical image of the first domain and the medical image of the second domain; and performing training processing of training the first generator and the first discriminator in an adversarial manner based on the plurality of pieces of training data.

A medical image processing apparatus according to still yet another aspect of the present disclosure, the apparatus comprises a second storage device that stores a first trained model which is the trained first generator trained by implementing the method of generating a trained model according to any aspect of the present disclosure, and a second processor that performs image processing using the first trained model, in which the first trained model is a model that receives an input of a first medical image and is trained to output a second medical image of a domain different from the first medical image.

According to the present invention, it is possible to improve robustness against a misregistration of data used for training, and even in a case where data of an image with a misregistration is used, it is possible to implement training of appropriate domain conversion. According to the present invention, it is possible to obtain a trained model that outputs an appropriate generated image of a different domain for an input medical image. In addition, by using the trained model generated by the present invention, it is possible to obtain a high-quality pseudo image (generated image) having a feature of a heterogeneous domain.

DESCRIPTION OF THE PREFERRED EMBODIMENTS

Hereinafter, a preferred embodiment of the present invention will be described in accordance with the appended drawings.

<<Description of Medical Image>>

A modality, such as a CT apparatus or an MRI apparatus, is exemplified as a representative example of an apparatus that captures a medical image. In these modalities, as a basic concept, three-dimensional data indicating a three-dimensional form of an object is obtained by continuously capturing two-dimensional slice images. In the present specification, the term "three-dimensional data" includes a concept of an aggregate of two-dimensional slice images continuously captured, and is synonymous with a three-dimensional image. The term "image" includes the meaning of image data. The aggregate of continuous two-dimensional slice images may be referred to as a "two-dimensional image sequence" or a "two-dimensional image series". The term "two-dimensional image" includes a concept of a two-dimensional slice image extracted from the three-dimensional data.

<<Problem in Modality Conversion of Medical Image>>

Figure 1:
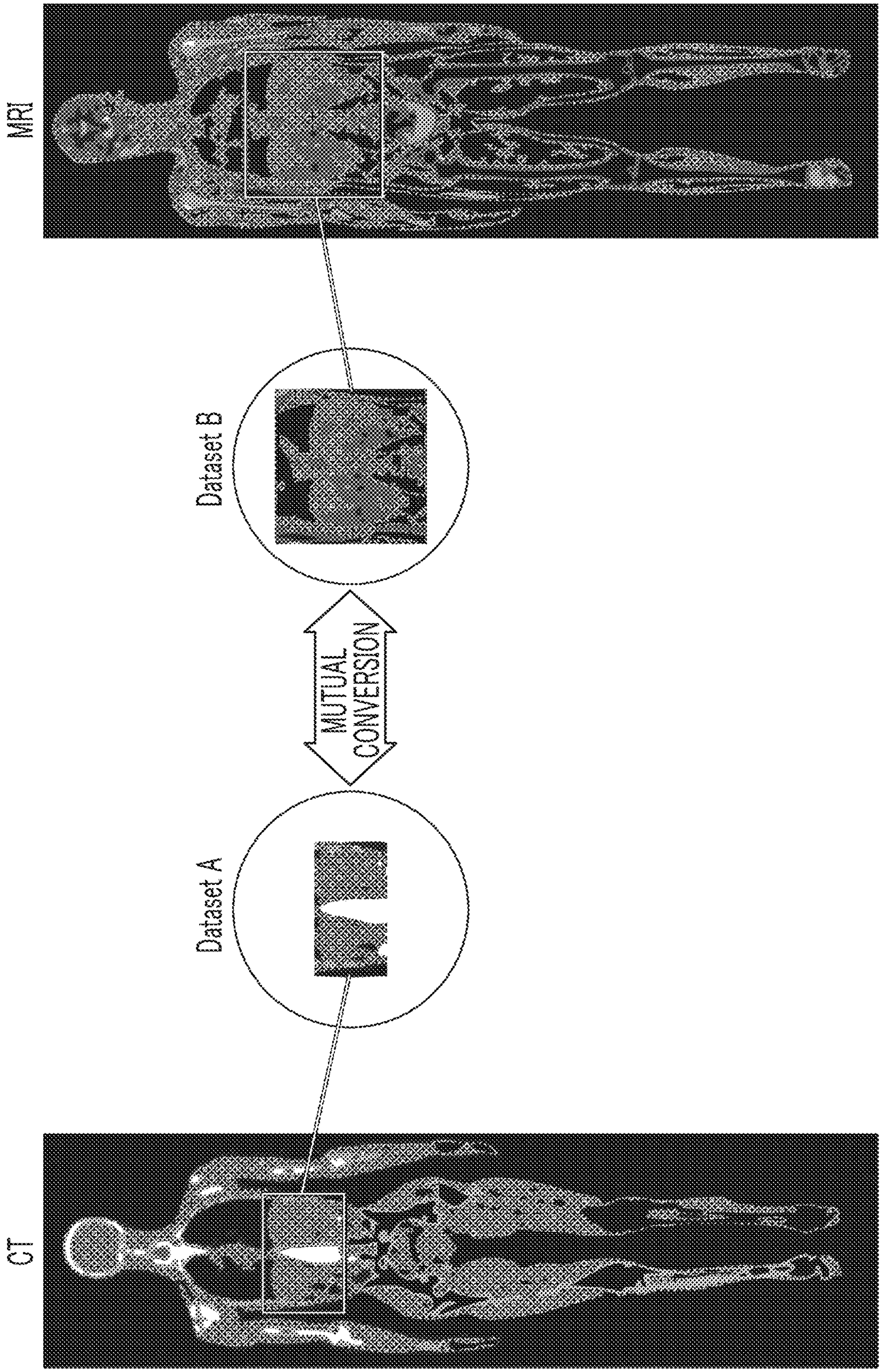
FIG. 1 is an explanatory diagram illustrating a problem in modality conversion of a medical image.

FIG. 1 is an explanatory diagram illustrating a problem in the modality conversion of the medical image. Here, an example of a case where a CT image and an MR image are used as training data and mutual conversion such as conversion from the CT image to the MR image and conversion from the MR image to the CT image is trained will be described. Each of the CT image and the MR image is three-dimensional data.

In a case where mutual conversion between CT and MR is trained using a dataset A in which a plurality of CT images are collected and a dataset B in which a plurality of MR images are collected, the positions of the images may be shifted between the datasets as illustrated in FIG. 1. It is difficult to directly train the task of modality conversion using the dataset of the image with such a misregistration. The description of "misregistration" includes the concepts of both a difference in the positions of the imaging regions and a difference in the sizes of the imaging regions. For example, in the case of the example illustrated in FIG. 1, since the imaging region of the MR image included in the dataset B is wider than the imaging region of the CT image included in the dataset A, there is a region that appears in the MR image but does not appear in the CT image.

Figure 2:
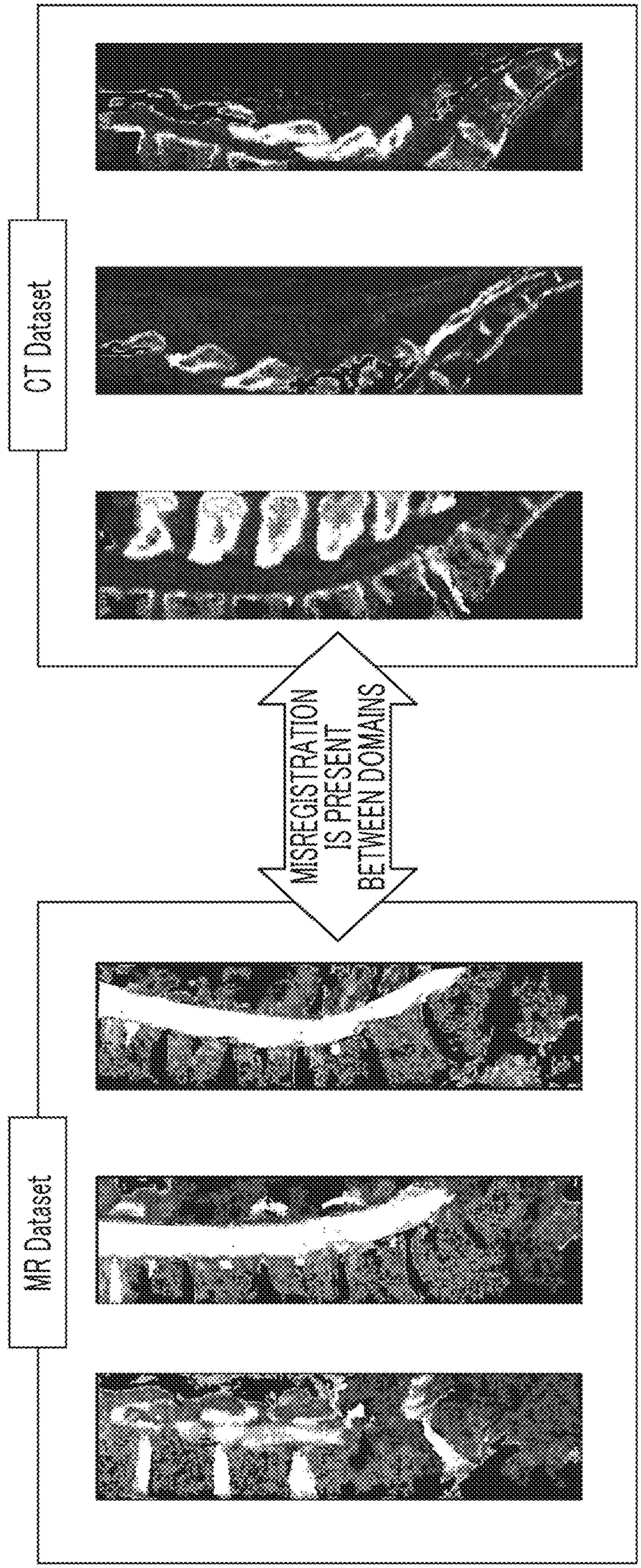
FIG. 2 is an example of an MR image included in a dataset of MR and a CT image included in a dataset of CT.
Figure 3:
FIG. 3 is an image example of MR-to-CT conversion.

Specific examples are illustrated in FIGS. 2 and 3. FIG. 2 is an example of the MR image included in the dataset of MR and the CT image included in the dataset of CT. As illustrated in FIG. 2, although the MR image and the CT image have a partial overlapping portion in the imaging region, there is a deviation in the imaging region, and the MR image captures a region wider than the CT image.

FIG. 3 illustrates an example of a generated image in a case where a generative adversarial network (GAN) according to Comparative Example is trained using a dataset in which there is the misregistration between domains as described above. The GAN according to Comparative Example has a configuration in which the network structure described in Jun-Yan Zhu, Taesung Park, Phillip Isola, Alexei A. Efros, "Unpaired Image-to-Image Translation using Cycle-Consistent Adversarial Networks", ArXiv: 1703.10593 is extended three-dimensionally.

FIG. 3 is an image example of MR-to-CT conversion, in which a left side is an MR image of a conversion source and a right side is a CT generated image after conversion. As illustrated in FIG. 3, in the CT generated image after the conversion, the misregistration of the dataset used for training is reflected as it is.

First Embodiment

Figure 4:
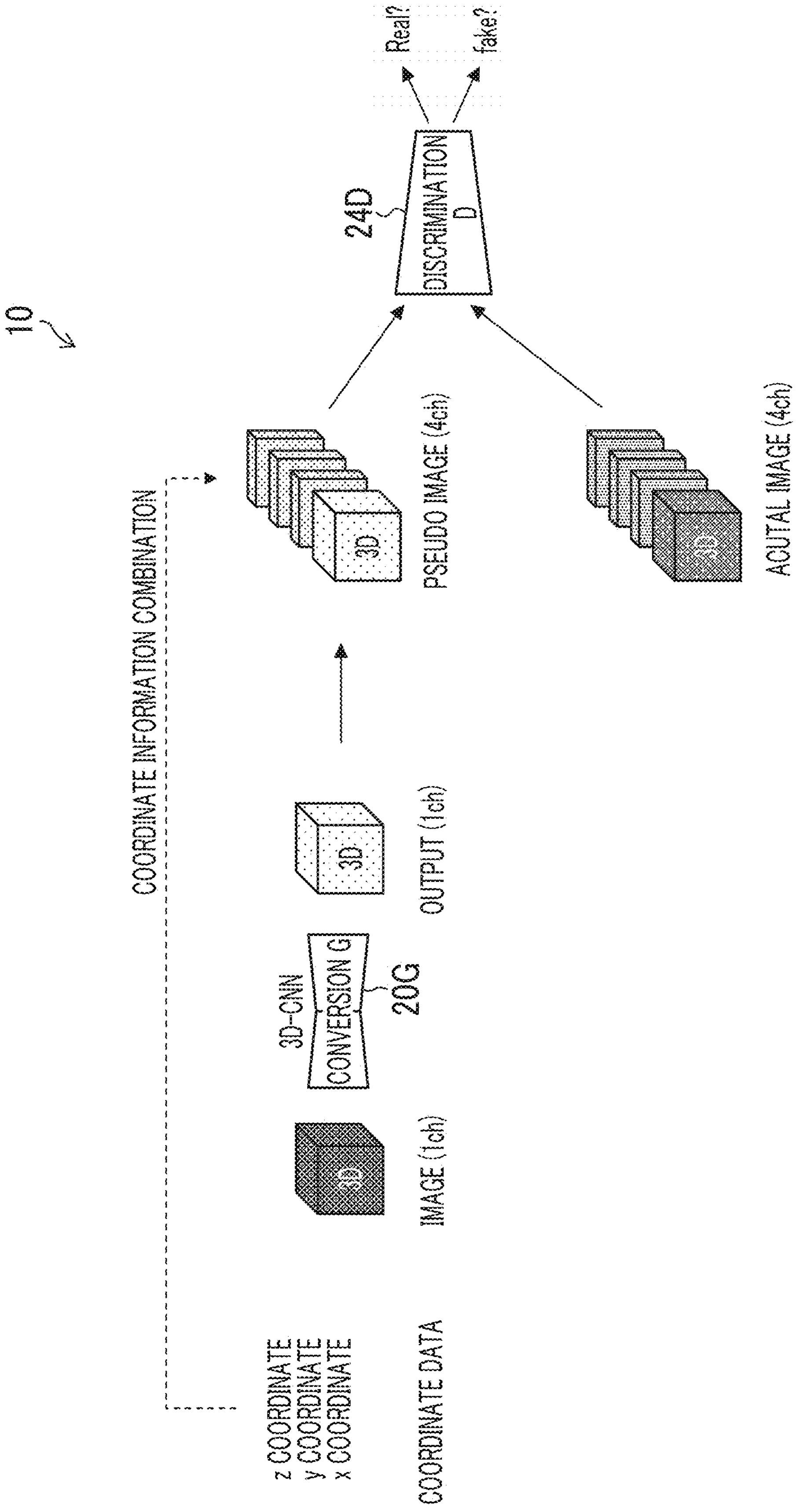
FIG. 4 is a conceptual diagram illustrating an outline of processing in a machine learning system according to a first embodiment.

FIG. 4 is a conceptual diagram illustrating an outline of processing in a machine learning system 10 according to a first embodiment. Here, a method of training an image conversion task of generating a pseudo MR image from a CT image based on the architecture of the GAN with a source domain as CT and a target domain as MR will be described.

The machine learning system 10 includes a generator 20G and a discriminator 24D. Each of the generator 20G and the discriminator 24D is configured using a three-dimensional convolutional neural network (CNN). The generator 20G is a three-dimensional generation network (3D generator) that receives an input of three-dimensional data having a feature of a CT domain and outputs three-dimensional data having a feature of an MR domain. For example, a V-net type architecture obtained by extending U-net in three dimensions is applied to the generator 20G.

The U-net is a neural network that is widely used for medical image segmentation and the like. As a document describing the U-net, for example, there is "Olaf Ronneberger, et al. "U-Net: Convolutional Networks for Biomedical Image Segmentation", MICCAI, 2015". In addition, as a document describing the V-net, for example, there is "Fausto Milletari, et. al. "V-Net: Fully Convolutional Neural Networks for Volumetric Medical Image Segmentation"".

The discriminator 24D is a three-dimensional discrimination network (3D discriminator) that discriminates the authenticity of the image. In the machine learning system 10 according to the first embodiment, the coordinate information of the human body coordinate system is added to the image used for training, and the coordinate data indicating the coordinate information of the human body coordinate system corresponding to the image region is added to the data input to the discriminator 24D. The coordinate information includes x coordinate information, y coordinate information, and z coordinate information that specify the position of each voxel constituting the image in a three-dimensional space.

That is, in the machine learning system 10, channels (3*ch*) of three coordinate data of an x coordinate, a y coordinate, and a z coordinate is added to the data input to the discriminator 24D, and data of 4*ch* in which a channel (lch) of the image and channels (3*ch*) of coordinates are combined is input to the discriminator 24D.

The generated image which is the pseudo MR image generated by the generator 20G or data including the image data of the actual MR image included in the training dataset and the coordinate information corresponding the image data are input to the discriminator 24D, and the authenticity discrimination of whether the image is a real image or a fake image generated by the generator 20G in the discriminator 24D. The image data input to the discriminator 24D is an example of "first image data" according to the embodiment of the present disclosure.

The "real image" means an actual image obtained by actually performing imaging using an imaging apparatus. The "fake image" means a generated image (pseudo image) artificially generated by image conversion processing without performing imaging. In the case of the first embodiment, the data used as the training data input to the learning model 44 is the "real image", and the generated image generated by the generator 20G is the "fake image".

Figure 5:
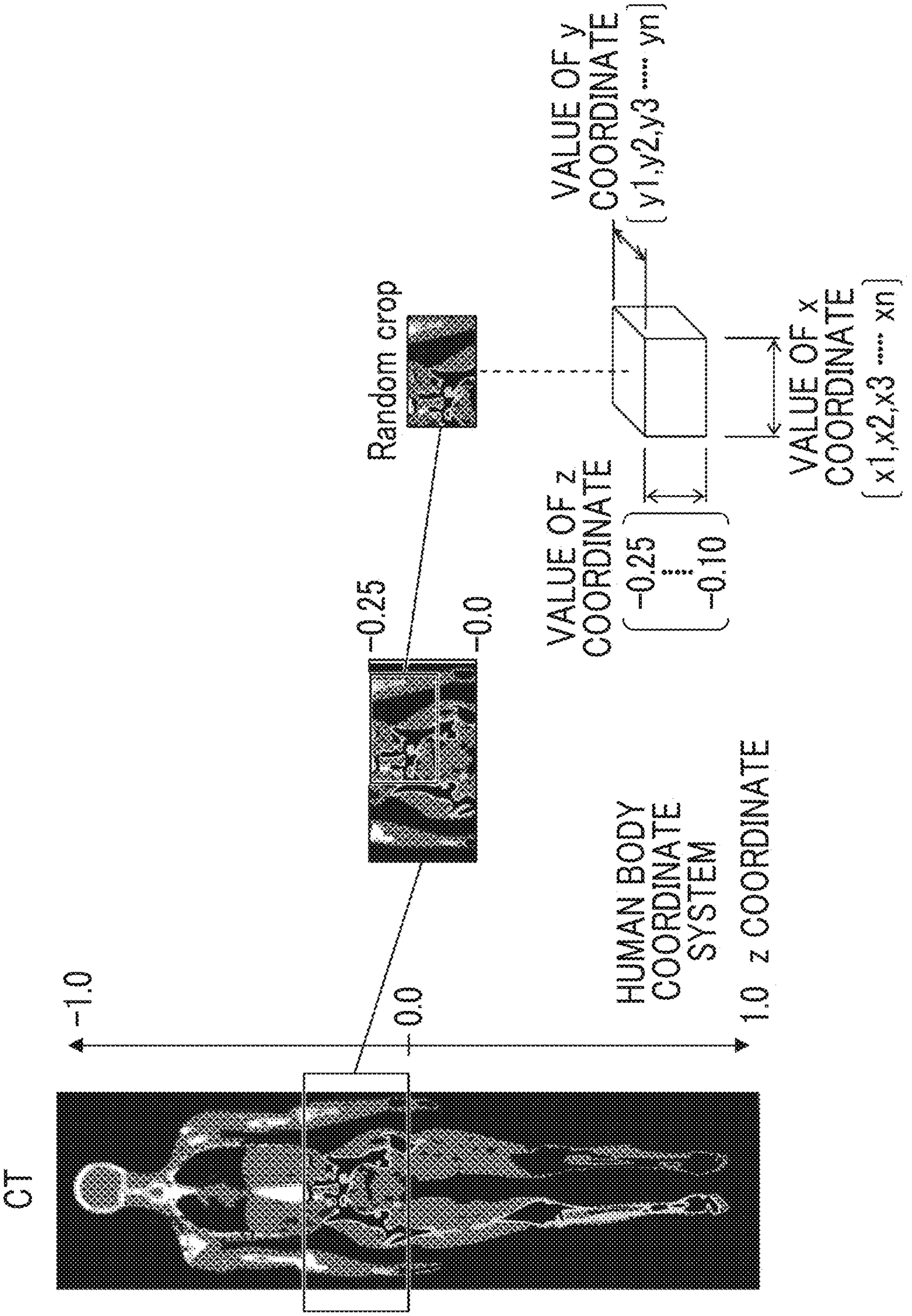
FIG. 5 is an explanatory diagram of a human body coordinate system applied to the first embodiment.

FIG. 5 is an explanatory diagram of the human body coordinate system applied to the first embodiment. In the present specification, a body axis direction is a z-axis direction, a horizontal direction (left-right direction) of a human body in a standing posture is an x-axis direction, and a depth direction (front-rear direction) is a y-axis direction. A coordinate system is defined in which a vertex side is "−1.0" and a toe side is "1.0" as z coordinate in the human body coordinate system. The x coordinate and the y coordinate are defined as "−1.0 to 1.0" within a range in which the whole human body is accommodated, like the z coordinate.

The definition of the human body coordinate system is not limited to this example, and as long as a coordinate system that can specify a spatial position as an absolute coordinate with reference to an anatomical position of a portion of the human body may be defined. That is, the human body coordinate system is the absolute coordinate defined with reference to the anatomical position of the portion of the human body, and a coordinate value of the human body coordinate system has meaning as a value of the absolute coordinate even between different images.

The data used for training can be generated, for example, by cutting out a part from an image (whole body image) obtained by imaging the whole body of the patient. In a case where there is a whole body image, an x coordinate, a y coordinate, and a z coordinate can be determined according to the above-described definition, and coordinate information can be associated with each voxel. In addition to the whole body image, for example, in a case where a partial image such as an upper body, chest, or pelvis is used, the value of each of the x coordinate, the y coordinate, and the z coordinate may be determined by specifying an anatomical landmark in the image and comparing the anatomical landmark with an anatomical atlas of a standard human body.

In a case where the data of the image region used for training is cropped from the original three-dimensional data, the coordinate information is also cropped, and thus the cropped three-dimensional data and the coordinate information corresponding thereto are associated (linked). The image region to be cropped may be randomly determined.

Figure 6:
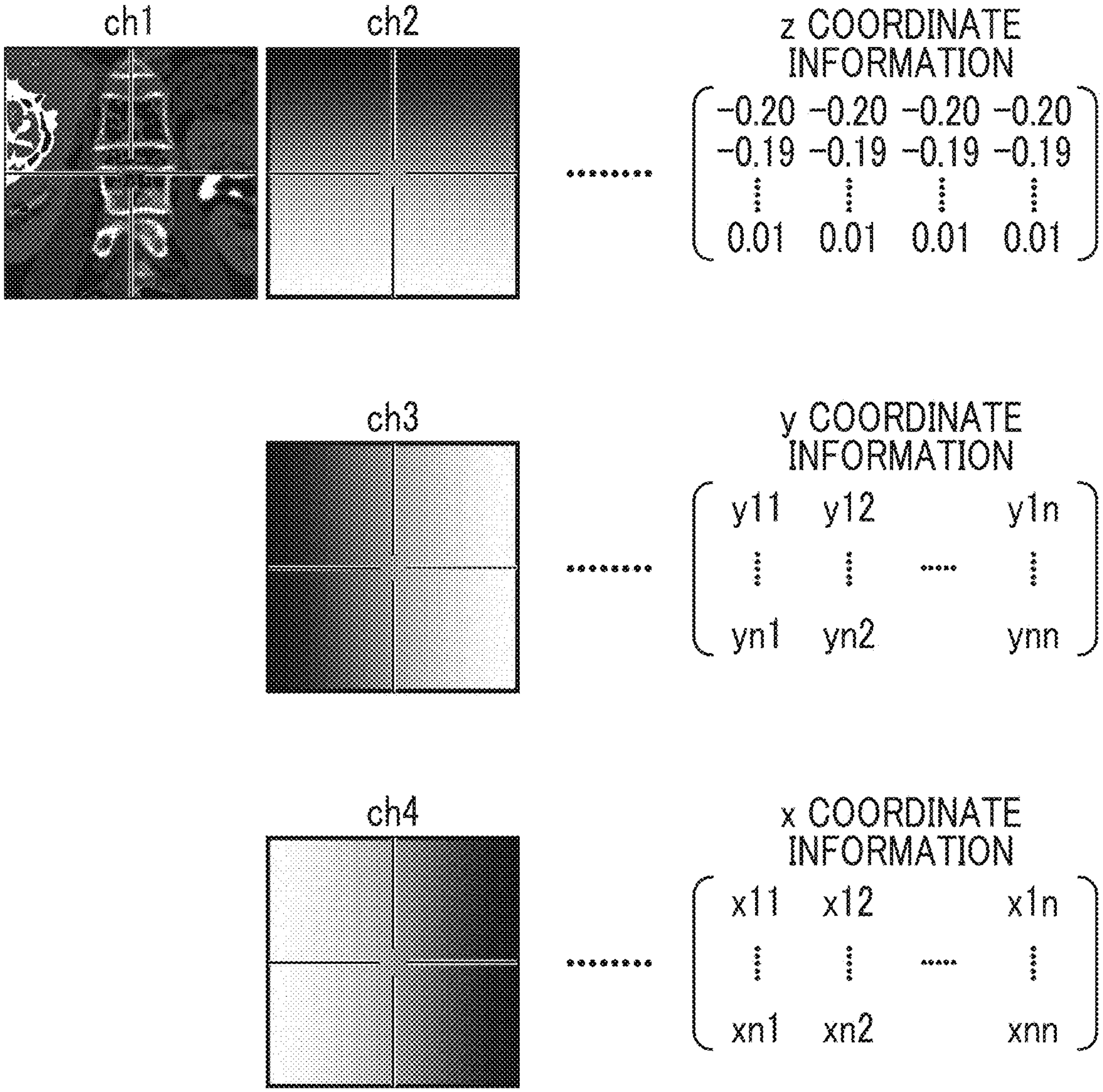
FIG. 6 illustrates an example of coordinate information added to an image.

FIG. 6 illustrates an example of coordinate information added to an image. Here, a channel of the image is illustrated as ch1, a channel of the z coordinate information is illustrated as ch2, a channel of the y coordinate information is illustrated as ch3, and a channel of the x coordinate information is illustrated as ch4. The coordinate information of each coordinate axis can be handled as image data by representing the coordinate value with gradation. Each of the coordinate channels ch2 to ch4 can be data corresponding to a gradation image in which the coordinate value is reflected.

Configuration Example of Machine Learning System 10

Figure 7:
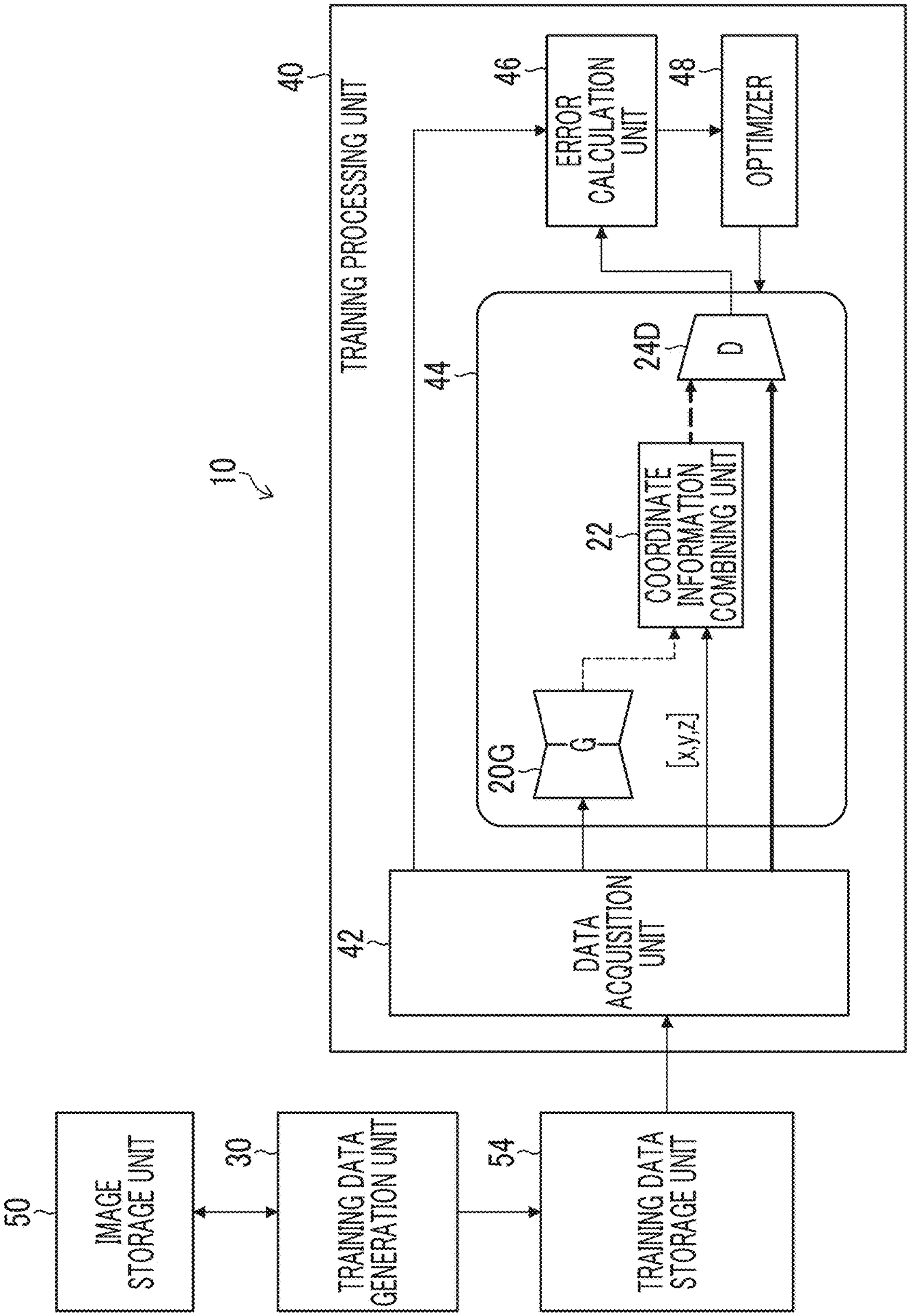
FIG. 7 is a functional block diagram illustrating a configuration example of the machine learning system according to the first embodiment.

FIG. 7 is a functional block diagram illustrating a configuration example of the machine learning system 10 according to the first embodiment. The machine learning system 10 includes a training data generation unit 30 and a training processing unit 40. The machine learning system 10 may further include an image storage unit 50 and a training data storage unit 54.

The machine learning system 10 can be implemented by a computer system including one or a plurality of the computers. Each function of the training data generation unit 30, the training processing unit 40, the image storage unit 50, and the training data storage unit 54 can be implemented by a combination of hardware and software of the computer. Functions of these units may be implemented by one computer, or may be implemented by two or more computers by sharing the processing functions.

Here, an example in which the training data generation unit 30, the training processing unit 40, the image storage unit 50, and the training data storage unit 54 are configured as separate devices will be described. For example, the training data generation unit 30, the training processing unit 40, the image storage unit 50, and the training data storage unit 54 may be connected to each other via an electric communication line. The term "connection" is not limited to a wired connection, and also includes a concept of wireless connection. The electric communication line may be a local area network or may be a wide area network. With this configuration, generation processing of the training data and the training processing of the generation model can be performed without being physically and temporally bound to each other.

The image storage unit 50 includes a large-capacity storage device that stores CT reconstructed images (CT images) captured by a medical X-ray CT apparatus and MR reconstructed images (MR images) captured by the MRI apparatus. The image storage unit 50 may be, for example, a digital imaging and communications in medicine (DICOM) server that stores medical images conforming to the DICOM standard. The medical image stored in the image storage unit 50 may be an image for each portion of a human body or may be an image obtained by imaging the whole body.

The training data generation unit 30 generates data for training (training data) used for machine learning. The training data is synonymous with "learning data". In the machine learning system 10, a dataset including a plurality of pieces of three-dimensional data which is an actual CT image actually captured using the CT apparatus and a dataset including a plurality of pieces of three-dimensional data which is an actual MR image actually captured using the MRI apparatus are used as the training data. Coordinate information for each voxel is attached to each three-dimensional data. Such training data can be generated from data stored in the image storage unit 50. The voxel is an example of a "unit element" according to the embodiment of the present disclosure.

The training data generation unit 30 acquires original three-dimensional data from the image storage unit 50, performs preprocessing such as generation of coordinate information and cutout (crop) of the fixed-size region, and generates three-dimensional data with coordinate information of a desired image size suitable for input to the training processing unit 40. In order to efficiently perform the training processing by the training processing unit 40, a plurality of pieces of training data may be generated in advance using the training data generation unit 30 and stored in a storage as the training dataset.

The training data storage unit 54 includes a storage that stores the pre-processed training data generated by the training data generation unit 30. The training data generated by the training data generation unit 30 is read out from the training data storage unit 54 and is input to the training processing unit 40.

The training data storage unit 54 may be included in the training data generation unit 30, or a part of the storage region of the image storage unit 50 may be used as the training data storage unit 54. In addition, a part or all of the processing functions of the training data generation unit 30 may be included in the training processing unit 40.

The training processing unit 40 includes a data acquisition unit 42 and a learning model 44 having a structure of GAN. The data acquisition unit 42 acquires training data to be input to the learning model 44 from the training data storage unit 54. The training data acquired via the data acquisition unit 42 is input to the learning model 44. The learning model 44 includes the generator 20G and the discriminator 24D. In addition, the training processing unit 40 includes a coordinate information combining unit 22 that combines coordinate information with the generated image output from the generator 20G. The coordinate information combining unit 22 combines the coordinate information associated with the input image that is the generation source (conversion source) of the generated image with the generated image and gives it to the discriminator 24D.

The training processing unit 40 further includes an error calculation unit 46 and an optimizer 48. The error calculation unit 46 evaluates an error between output from the discriminator 24D and a correct answer using a loss function. The error may be rephrased as a loss.

The optimizer 48 performs processing of updating parameters of the network in the learning model 44 based on a calculation result of the error calculation unit 46. The parameters of the network include a filter coefficient (weight of connection between nodes) of filters used for processing each layer of the CNN, a bias of a node, and the like.

That is, the optimizer 48 performs parameter calculation processing of calculating the update amount of the parameter of each network of the generator 20G and the discriminator 24D from the calculation result of the error calculation unit 46 and parameter update processing of updating the parameter of each network of the generator 20G and the discriminator 24D according to the calculation result of the parameter calculation processing. The optimizer 48 performs updating of the parameters based on an algorithm such as a gradient descent method.

The training processing unit 40 trains the learning model 44 to improve the performance of each network by repeating the adversarial training using the generator 20G and the discriminator 24D based on the input training data.

<<About Generation of Training Data>>

Figure 8:
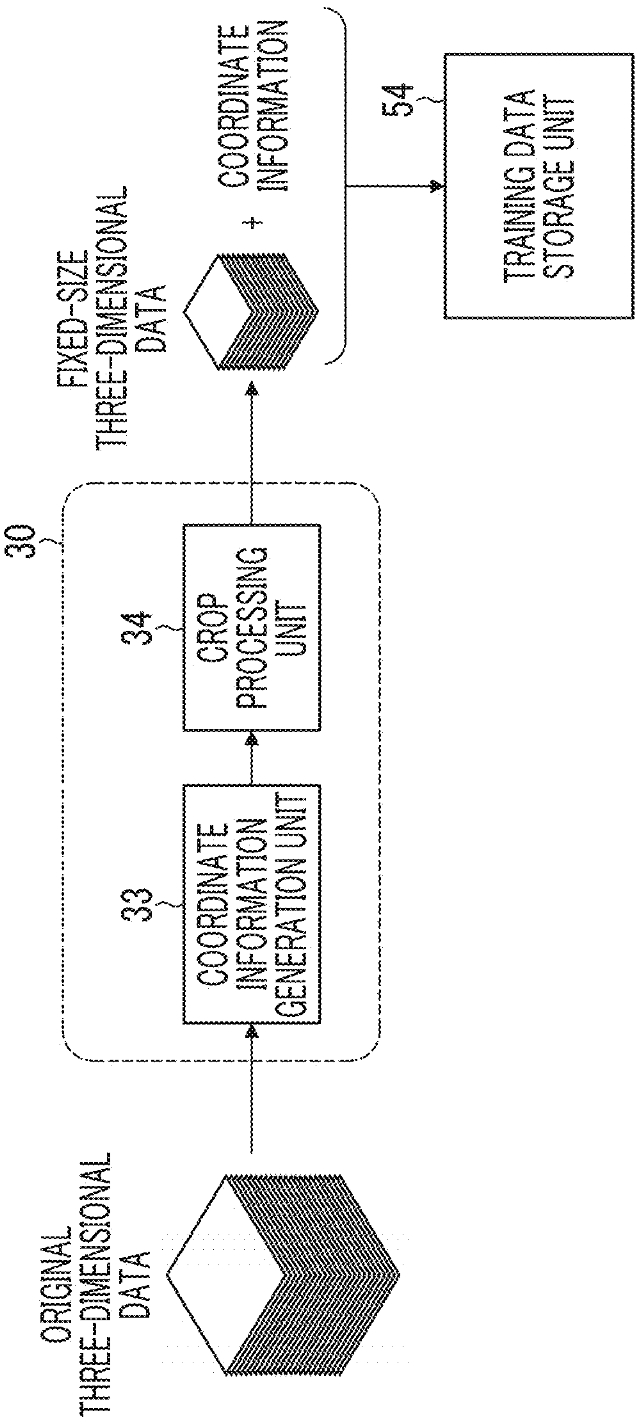
FIG. 8 is a functional block diagram illustrating a configuration example of a training data generation unit.

FIG. 8 is a functional block diagram illustrating a configuration example of the training data generation unit 30. The training data generation unit 30 includes a coordinate information generation unit 33 and a crop processing unit 34. The coordinate information generation unit 33 performs processing of generating coordinate information of the human body coordinate system for the position of each voxel in original three-dimensional data (original three-dimensional image) to be processed. The coordinate information generation unit 33 assigns a coordinate value of the human body coordinate system to each voxel of the original three-dimensional image in accordance with the definition of the human body coordinate system described in FIG. 5.

The crop processing unit 34 performs processing of randomly cutting out a fixed-size region from the original three-dimensional image to which coordinate information is attached. In a case of cropping the image region, the crop processing unit 34 also crops the coordinate information. The three-dimensional data cut out to the fixed-size region by the crop processing unit 34 is associated with the coordinate information and is stored in the training data storage unit 54.

The original three-dimensional data input to the training data generation unit 30 may be the CT image or may be the MR image. The cropped fixed-size three-dimensional data may be understood as the training data, or the original three-dimensional data before being cropped may be understood as the training data.

Training Method According to First Embodiment

The data used for training in the first embodiment may be a dataset for each domain as described in FIG. 1, and the data may be randomly extracted from the dataset of each domain. The machine learning system 10 according to the first embodiment does not exclude the possibility of training using pair images. For example, training using, as training data, pair images obtained by imaging the same imaging region with different modalities is also possible.

In the machine learning system 10 according to the first embodiment, in a case where image data is input to the discriminator 24D, coordinate data corresponding to the image data is input. In a case where the generated image (pseudo image) generated by the generator 20G is input to the discriminator 24D, the coordinate data corresponding to the generated image is the coordinate data determined for the conversion source image input to the generator 20G. On the other hand, in a case where the actual image included in the training dataset is input to the discriminator 24D, the coordinate data associated with the actual image is input to the discriminator 24D.

The discriminator 24D performs convolution on the input image data and coordinate data and performs the authenticity discrimination. The adversarial training is performed on the generator 20G and the discriminator 24D by the algorithm of the GAN, and the discriminator 24D is trained to discriminate the authenticity according to the position indicated by the coordinate information. According to the first embodiment, it is possible to implement image conversion robust against the misregistration between datasets.

The method of generating the trained generator 20G by the training processing using the machine learning system 10 is an example of a "method of generating a trained model" according to the embodiment of the present disclosure. The generator 20G is an example of a "first generator" according to the embodiment of the present disclosure, and the three-dimensional CNN used for the generator 20G is an example of a "first convolutional neural network" according to the embodiment of the present disclosure. The discriminator 24D is an example of a "first generator" according to the embodiment of the present disclosure, and the three-dimensional CNN used for the discriminator 24D is an example of a "second convolutional neural network" according to the embodiment of the present disclosure. The domain of CT is an example of a "first domain" according to the embodiment of the present disclosure, and the domain of MR is an example of a "second domain" according to the embodiment of the present disclosure. The CT image input to the generator 20G is an example of a "medical image of the first domain" and a "first modality image" according to the embodiment of the present disclosure. The pseudo MR image generated by the generator 20G is an example of a "first generated image" according to the embodiment of the present disclosure. The pseudo MR image output from the generator 20G is an example of a "second modality generated image" according to the embodiment of the present disclosure. Each of the CT apparatus and the MRI apparatus is an example of a "medical apparatus" according to the embodiment of the present disclosure. The CT apparatus is an example of a "first modality" according to the embodiment of the present disclosure, and the MM apparatus is an example of a "second modality" according to the embodiment of the present disclosure. The MR image that is the actual image input to the discriminator 24D is an example of a "medical image of the second domain" and a "second modality image" according to the embodiment of the present disclosure.

Figure 9:
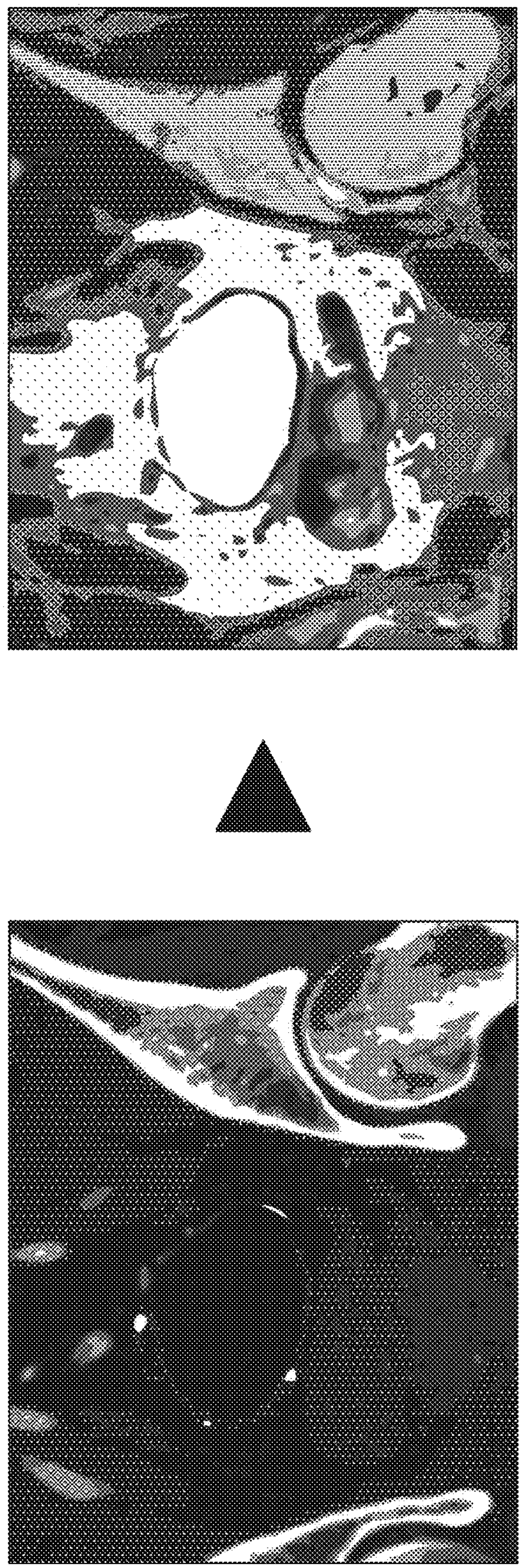
FIG. 9 is an example of a pseudo MR image generated by a trained model which is trained by the training processing using the machine learning system according to the first embodiment.

FIG. 9 is an example of a pseudo MR image generated by a trained model which is trained by the training processing using the machine learning system 10 according to the first embodiment. A CT image of a conversion source is illustrated on the left side, and a pseudo MR image after conversion is illustrated on the right side. The pseudo MR image after the conversion output from the trained model is an image of the same portion as the input CT image. As a result of training according to the first embodiment, as illustrated in FIG. 9, the trained model can appropriately generate a pseudo MR image without the misregistration by converting the domain from the CT image.

Modification Example 1

In the first embodiment, an example in which the four channels obtained by combining the image channels and the coordinate channels are input to the input layer of the discriminator 24D is illustrated, but the coordinate information may be input to any layer of the interlayers in the CNN constituting the discriminator 24D. In this case, the coordinate data is given to the discriminator 24D by performing processing such as pooling on the original coordinate data, adjusting the number of voxels being the same as that of the feature map of the image data, and combining the coordinate channels with the channels of the feature map.

Modification Example 2

In the first embodiment, an example in which the three-dimensional CNN for the three-dimensional image is used has been described, but a two-dimensional CNN for a two-dimensional image can be applied. Even in a case of the two-dimensional image, the definition of the human body coordinate system is the same as that in the case of the three-dimensional image, and the coordinate information for the two-dimensional image may be two-dimensional coordinate data corresponding to each pixel constituting the image.

Second Embodiment

In the second embodiment, an example in which an architecture based on the mechanism of CycleGAN described in Zizhao Zhang, Lin Yang, Yefeng Zheng "Translating and Segmenting Multimodal Medical Volumes with Cycle- and Shape-Consistency Generative Adversarial Network", ArXiv: 1802.09655 is adopted, and an image group of each domain having no correspondence relationship (not paired) is used as the training data to train a task of domain conversion.

Figure 10:
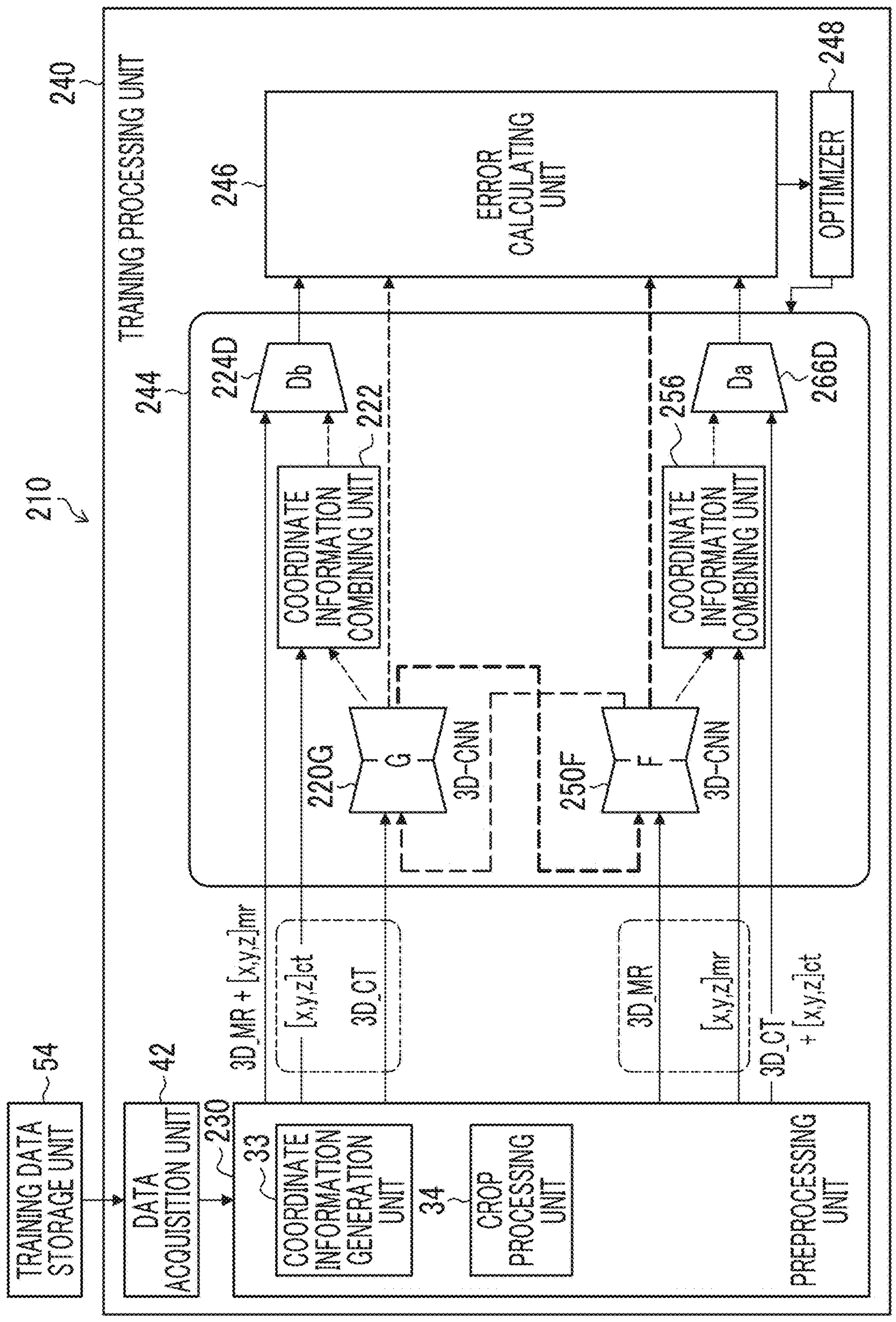
FIG. 10 is a functional block diagram illustrating a configuration example of a machine learning system according to a second embodiment.

FIG. 10 is a functional block diagram illustrating a configuration example of a machine learning system 210 according to the second embodiment. In FIG. 10, elements that are the same as or similar to those in the configuration illustrated in FIG. 6 are denoted by the same reference numerals, and redundant descriptions thereof will be omitted.

The training data storage unit 54 illustrated in FIG. 10 stores original three-dimensional data belonging to the respective domains of CT and MR.

The machine learning system 210 includes a training processing unit 240 instead of the training processing unit 40 in FIG. 6. The training processing unit 240 includes a data acquisition unit 42, a preprocessing unit 230, a learning model 244, an error calculation unit 246, and an optimizer 248.

The preprocessing unit 230 performs the same processing as the training data generation unit 30 described with reference to FIG. 8, and includes the coordinate information generation unit 33 and the crop processing unit 34. The preprocessing unit 230 performs preprocessing for input to the learning model 244 on the three-dimensional data acquired via the data acquisition unit 42. Here, the coordinate information generation processing and the crop processing are exemplified as the preprocessing, but these processing may be performed as necessary, and a part or all of the processing in the preprocessing unit 230 may be omitted.

For example, as described in FIG. 8, the preprocessing may be performed in advance, and the preprocessed dataset may be stored in the training data storage unit 54. In addition, the preprocessing unit 230 may be configured separately with a preprocessing unit for CT that performs preprocessing of a CT image and a preprocessing unit for MR that performs preprocessing of an MR image.

The learning model 244 includes a first generator 220G, a coordinate information combining unit 222, a first discriminator 224D, a second generator 250F, a coordinate information combining unit 256, and a second discriminator 266D.

Each of the first generator 220G and the second generator 250F is configured using the three-dimensional CNN. The network structure of each of the first generator 220G and the second generator 250F may be the same as that of the generator 20G described in the first embodiment.

The network structure of each of the first discriminator 224D and the second discriminator 266D may be the same as that of the discriminator 24D described in the first embodiment.

The first generator 220G is a 3D generator that performs CT-to-MR domain conversion, receives an input of three-dimensional data having a feature of a CT domain, and generates and outputs three-dimensional data having a feature of an MR domain. In FIG. 10, the description "3D_CT" input to the first generator 220G represents three-dimensional data of the actual CT image.

The coordinate information combining unit 222 combines the channel (3*ch*) of the coordinate information with the pseudo MR image generated by the first generator 220G. The coordinate information to be combined with the pseudo MR image is coordinate information attached to the actual CT image which is an original input image before the conversion. The description "[x, y, z] ct" in FIG. 10 represents coordinate information attached to the actual CT image before the conversion.

The first discriminator 224D is an MR discriminator that discriminates the authenticity of an image related to the domain of MR. That is, in the first discriminator 224D, data in which the pseudo MR image generated by the first generator 220G and coordinate information corresponding to the pseudo MR image are combined or data in which an actual MR image that is training data and coordinate information corresponding to the actual MR image are combined is input, and the authenticity discrimination of whether the image is a real image or a fake image generated by the first generator 220G in the first discriminator 224D. The description of "3D_MR+[x, y, z] mr" in FIG. 10 represents data of four channels in which the actual MR image that is the training data and coordinate information corresponding the actual MR image are combined.

The second generator 250F is a 3D generator that performs MR-to-CT domain conversion, receives an input of three-dimensional data having an MR domain feature, and generates and outputs three-dimensional data having a feature of a CT domain. In FIG. 10, the description "3D_MR" input to the second generator 250F represents three-dimensional data of the actual MR image.

The coordinate information combining unit 256 combines the channel (3*ch*) of the coordinate information with the pseudo CT image generated by the second generator 250F. The coordinate information to be combined with the pseudo CT image is coordinate information attached to the actual MR image which is an original input image before the conversion. The description "[x, y, z] mr" in FIG. 10 represents coordinate information attached to the actual MR image before the conversion.

The second discriminator 266D is a CT discriminator that discriminates the authenticity of an image related to the domain of CT. That is, in the second discriminator 266D, data in which the pseudo CT image and coordinate information corresponding to the pseudo CT image are combined or data in which an actual CT image that is training data and coordinate information corresponding to the actual CT image are combined is input, and the authenticity discrimination of whether the image is a real image or a fake image generated by the second generator 250F in the second discriminator 266D. The description of "3D_CT+[x, y, z] ct" in FIG. 10 represents data of four channels in which the actual CT image that is the training data and coordinate information corresponding the actual CT image are combined.

In addition, the output of the first generator 220G may be input to the second generator 250F. The image after the CT-to-MR conversion by the first generator 220G is further subjected to MR-to-CT conversion by the second generator 250F, so that a reconstructed generated image (reconstructed pseudo CT image) is generated. Similarly, the output of the second generator 250F may be input to the first generator 220G. The image after the MR-to-CT conversion by the second generator 250F is further subjected to CT-to-MR conversion by the first generator 220G to generate a reconstructed generated image (reconstructed pseudo MR image).

The error calculation unit 246 evaluates an error (adversarial loss) between an output from each discriminator (224D and 226D) and a correct answer using a loss function. Further, the error calculation unit 246 evaluates a reconstruction loss (cycle consistency loss) through image conversion in which the first generator 220G and the second generator 250F are connected.

The reconstruction loss includes an error between the reconstructed generated image output from the second generator 250F by inputting the output of the CT-to-MR conversion by the first generator 220G to the second generator 250F and the original input image input to the first generator 220G (reconstruction loss through CT-to-MR-to-CT conversion), and an error between the reconstructed generated image output from the first generator 220G by inputting the output of the MR-to-CT conversion by the first generator 220G to the second generator 250F and the original input image input to the second generator 250F (reconstruction loss through MR-to-CT-to-MR conversion).

The optimizer 248 performs processing of updating parameters of the network in the learning model 244 based on a calculation result of the error calculation unit 246. The optimizer 248 performs parameter calculation processing of calculating the update amount of the parameter of each network of the first generator 220G, the first discriminator 224D, the second generator 250F and the second discriminator 266D from the calculation result of the error calculation unit 46, and parameter update processing of updating the parameter of each network according to the calculation result of the parameter calculation processing.

<Outline of Processing at the Time of CT Input (CT-to-MR)>

Figure 11:
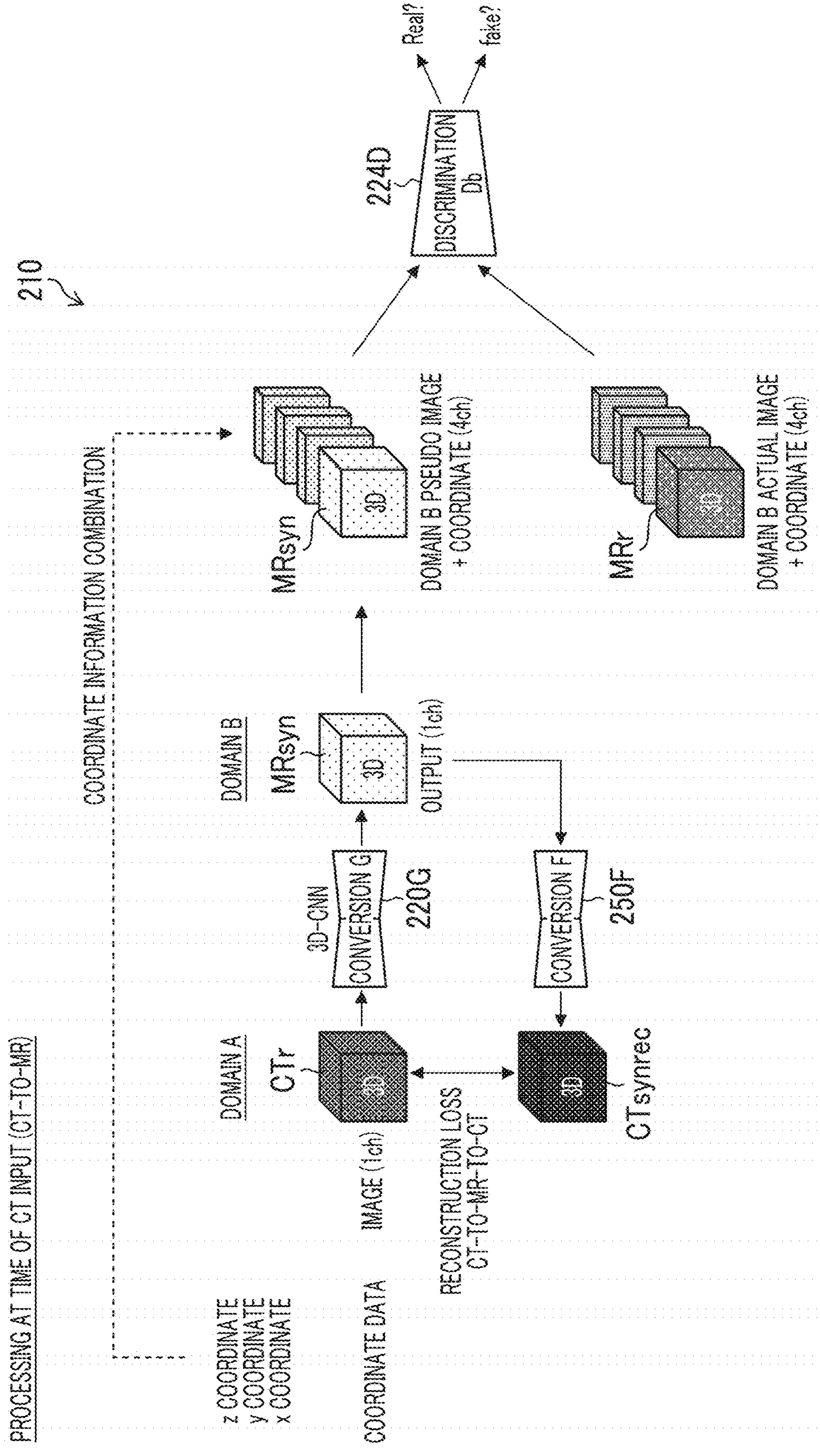
FIG. 11 is a schematic diagram illustrating a processing flow at the time of CT input in the machine learning system according to the second embodiment.

FIG. 11 is a schematic diagram illustrating a processing flow at the time of CT input in the machine learning system 210 according to the second embodiment. A CT image CTr which is three-dimensional data belonging to the training dataset of a domain A is input to the first generator 220G. The first generator 220G receives the input of the CT image CTr, performs CT-to-MR conversion, and outputs a pseudo MR image MRsyn having a feature of a domain B.

The coordinate information including each coordinate data of the x coordinate, the y coordinate, and the z coordinate associated with the CT image CTr of the conversion source is combined with the pseudo MR image MRsyn as a new channel, and data of four channels including the pseudo MR image MRsyn and the coordinate information is input to the first discriminator 224D. In addition, data of four channels including the MR image MRr as the actual image and the coordinate information thereof is input to the first discriminator 224D. The MR image MRr is the three-dimensional data belonging to the training dataset of the domain B. The MR image MRr and coordinate information including each coordinate data of the x coordinate, the y coordinate, and the z coordinate associated with the MR image MRr are combined and input to the first discriminator 224D. The first discriminator 224D performs convolution on the input data of four channels and performs the authenticity discrimination of the image. The adversarial loss is calculated based on a discrimination result of the first discriminator 224D.

In addition, the pseudo MR image MRsyn generated by the first generator 220G is further input to the second generator 250F, and the second generator 250F receives the input of the pseudo MR image MRsyn, performs MR-to-CT conversion, and outputs a reconstructed pseudo CT image CTsynrec having the feature of the domain A.

In the machine learning system 210, a reconstruction loss indicating a difference between the reconstructed pseudo CT image CTsynrec output from the second generator 250F and the original CT image CTr is evaluated. The reconstruction loss is an example of a "first reconstruction loss" according to the embodiment of the present disclosure.

The reconstructed pseudo CT image CTsynrec generated by the conversion processing using the first generator 220G and the second generator 250F in this order is an example of a "first reconstructed generated image" according to the embodiment of the present disclosure.

<Outline of Processing at the Time of MR Input (MR-to-CT)>

Figure 12:
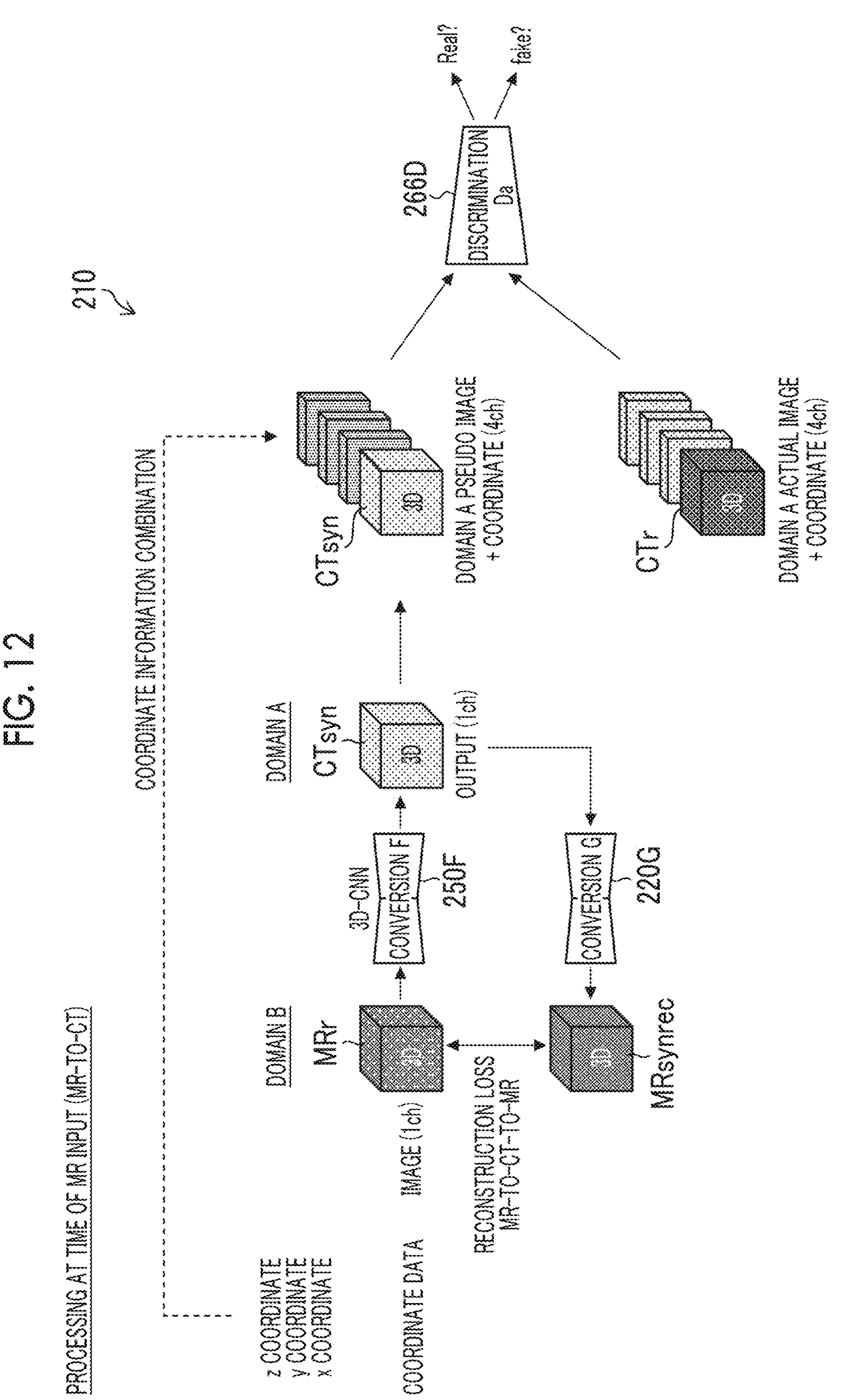
FIG. 12 is a schematic diagram illustrating a processing flow at the time of MR input in the machine learning system according to the second embodiment.

FIG. 12 is a schematic diagram illustrating a processing flow at the time of MR input in the machine learning system 210 according to the second embodiment. The MR image MRr, which is the three-dimensional data belonging to the training dataset of the domain B, is input to the second generator 250F. The second generator 250F receives the input of the CT image CTr, performs CT-to-MR conversion, and outputs a pseudo CT image CTsyn having the feature of the domain A.

The coordinate information including each coordinate data of the x coordinate, the y coordinate, and the z coordinate associated with the MR image MRr of the conversion source is combined with the pseudo CT image CTsyn as a new channel, and data of four channels including the pseudo CT image CTsyn and the coordinate information is input to the second discriminator 266D. In addition, data of four channels including the CT image CTr as the actual image and the coordinate information thereof is input to the second discriminator 266D. The CT image CTr is the three-dimensional data belonging to the training dataset of the domain A. The CT image CTr and coordinate information including each coordinate data of the x coordinate, the y coordinate, and the z coordinate associated with the CT image CTr are combined and input to the second discriminator 266D. The second discriminator 266D performs convolution on the input data of four channels and performs the authenticity discrimination of the image. The adversarial loss is calculated based on a discrimination result of the second discriminator 266D.

In addition, the pseudo CT image CTsyn generated by the second generator 250F is further input to the first generator 220G, and the first generator 220G receives the input of the pseudo CT image CTsyn, performs CT-to-MR conversion, and outputs a reconstructed pseudo MR image MRsynrec having the feature of the domain B.

In the machine learning system 210, a reconstruction loss indicating a difference between the reconstructed pseudo MR image MRsynrec output from the first generator 220G and an original MR image MRr is evaluated. The reconstruction loss is an example of a "second reconstruction loss" according to the embodiment of the present disclosure. The reconstructed pseudo MR image MRsynrec generated by the conversion processing using the second generator 250F and the first generator 220G in this order is an example of a "second reconstructed generated image" according to the embodiment of the present disclosure.

The three-dimensional CNN used for the second generator 250F of the second embodiment is an example of a "third convolutional neural network" according to the embodiment of the present disclosure. The pseudo CT image CTsyn generated by the second generator 250F is an example of a "second generated image" according to the embodiment of the present disclosure. The three-dimensional CNN used for the second discriminator 266D is an example of a "fourth convolutional neural network" according to the embodiment of the present disclosure. The image data input to the second discriminator 266D is an example of "second image data" according to the embodiment of the present disclosure.

Effect of Second Embodiment

By performing training using the machine learning system 210 according to the second embodiment, the first generator 220G can serve as a three-dimensional image converter that acquires the image generation capability of CT-to-MR conversion and generates a high-quality pseudo MR image. Similarly, the second generator 250F can serve as a three-dimensional image converter that acquires the image generation capability of MR-to-CT conversion and generates a high-quality pseudo CT image.

Configurati on Example of Machine Learning System

Figure 13:
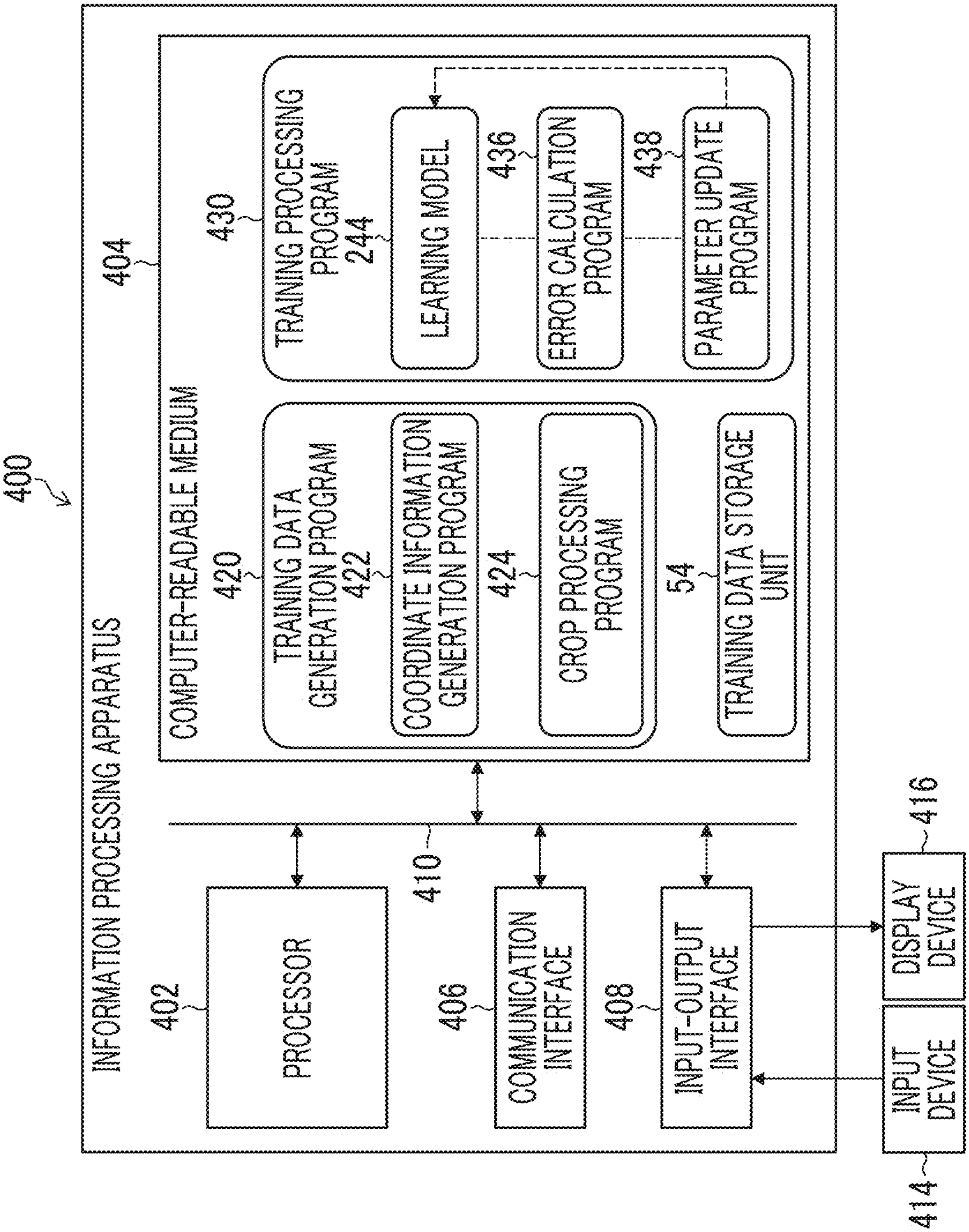
FIG. 13 is a block diagram illustrating a configuration example of an information processing apparatus applied to the machine learning system.

FIG. 13 is a block diagram illustrating a configuration example of an information processing apparatus 400 applied to the machine learning systems 10 and 210. The information processing apparatus 400 comprises a processor 402, a non-transitory tangible computer-readable medium 404, a communication interface 406, an input-output interface 408, a bus 410, an input device 414, and a display device 416. The processor 402 is an example of a "first processor" according to the embodiment of the present disclosure. The computer-readable medium 404 is an example of a "first storage device" according to the embodiment of the present disclosure.

The processor 402 includes a central processing unit (CPU). The processor 402 may include a graphics processing unit (GPU). The processor 402 is connected to the computer-readable medium 404, the communication interface 406, and the input-output interface 408 via the bus 410. The input device 414 and the display device 416 are connected to the bus 410 via the input-output interface 408.

The computer-readable medium 404 includes a memory that is a main memory, and a storage that is an auxiliary storage device. For example, the computer-readable medium 404 may be a semiconductor memory, a hard disk drive (HDD) device, or a solid state drive (SSD) device, or a combination of a plurality thereof.

The information processing apparatus 400 is connected to an electric communication line (not illustrated) via the communication interface 406. The electric communication line may be a wide area communication line, a private communication line, or a combination thereof.

The computer-readable medium 404 stores a plurality of programs for performing various types of processing, data, and the like. For example, a training data generation program 420 and a training processing program 430 are stored in the computer-readable medium 404. The training data generation program 420 may include a coordinate information generation program 422 and a crop processing program 424. The training processing program 430 may include the learning model 244, an error calculation program 436, and a parameter update program 438. Instead of the learning model 244, the learning model 44 may be used. The training data generation program 420 may be incorporated in the training processing program 430.

By executing instructions of the programs via the processor 402, the information processing apparatus 400 including the processor 402 functions as processing units corresponding to the programs. For example, the processor 402 executes the instructions of the coordinate information generation program 422, so that the processor 402 functions as the coordinate information generation unit 33 that generates the coordinate information of the human body coordinate system. In addition, by executing instructions of the training processing program 430 via the processor 402, the processor 402 functions as the training processing units 40 and 240 that perform training processing. The same applies to the other programs. A part of the storage region of the computer-readable medium 404 may function as the training data storage unit 54.

In addition, the computer-readable medium 404 stores a display control program (not illustrated). The display control program generates a display signal necessary for a display output to the display device 416 and performs a display control of the display device 416.

For example, the display device 416 is composed of a liquid crystal display, an organic electro-luminescence (OEL) display, or a projector, or an appropriate combination thereof. For example, the input device 414 is composed of a keyboard, a mouse, a multi-touch panel, other pointing devices, a voice input device, or an appropriate combination thereof. The input device 414 receives various inputs from an operator.

Example of Medical Image Processing Apparatus Using Trained Model

Figure 14:
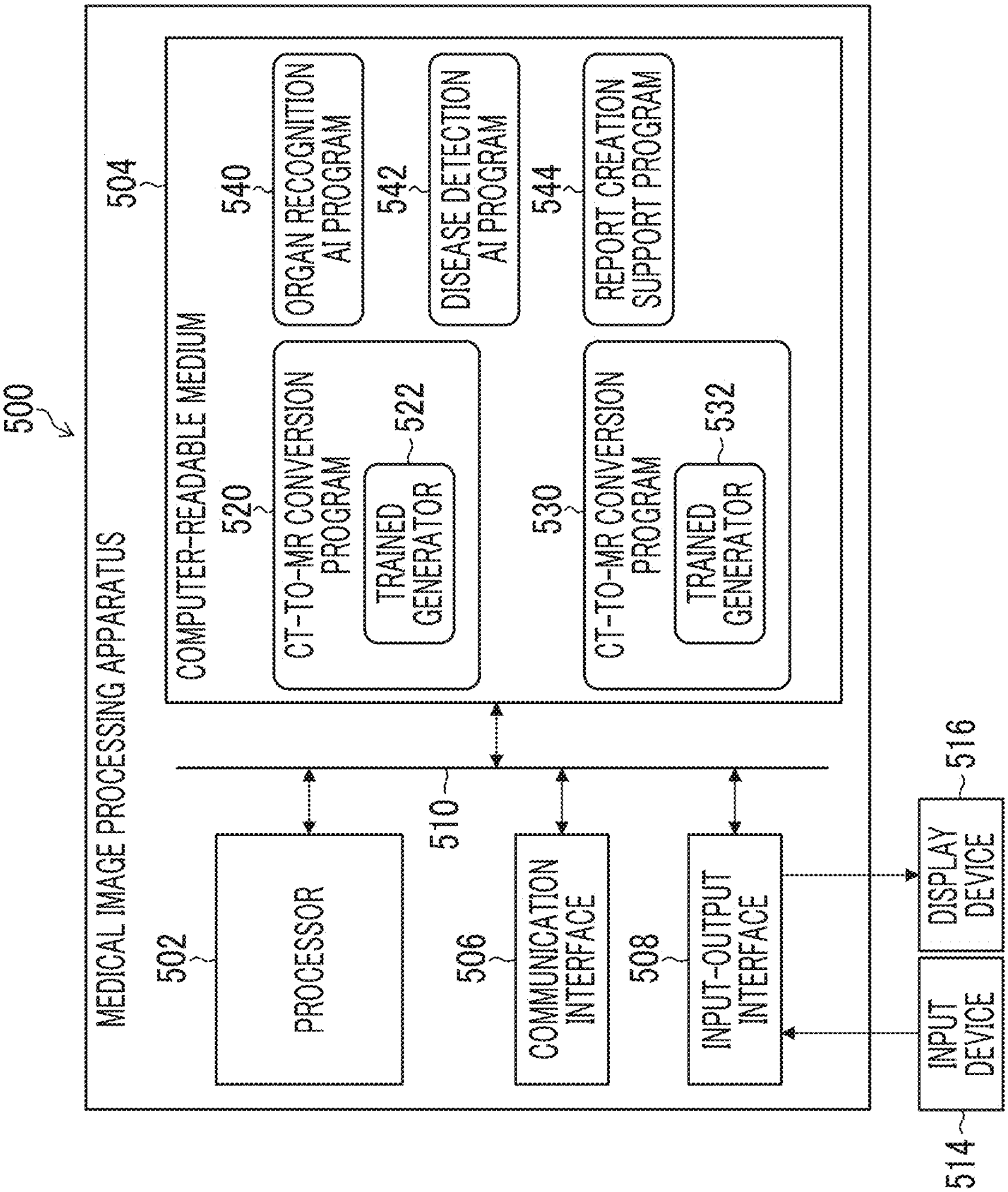
FIG. 14 is a block diagram illustrating a configuration example of a medical image processing apparatus to which a trained model generated by performing training processing using the machine learning systems is applied.

FIG. 14 is a block diagram illustrating a configuration example of a medical image processing apparatus 500 to which a trained model generated by performing training processing using the machine learning systems 10 and 210 is applied.

The medical image processing apparatus 500 comprises a processor 502, a non-transitory tangible computer-readable medium 504, a communication interface 506, an input-output interface 508, a bus 510, an input device 514, and a display device 516.

The hardware configurations of the processor 502, the computer-readable medium 504, the communication interface 506, the input-output interface 508, the bus 510, the input device 514, the display device 516, and the like may be the same as the corresponding elements of the processor 402, the computer-readable medium 404, the communication interface 406, the input-output interface 408, the bus 410, the input device 414, and the display device 416 in the information processing apparatus 400 described in FIG. 13. The processor 502 is an example of a "second processor" according to the embodiment of the present disclosure. The "computer-readable medium 504" is an example of a "second storage device" according to the embodiment of the present disclosure.

The computer-readable medium 504 of the medical image processing apparatus 500 stores at least one of a CT-to-MR conversion program 520 or an MR-to-CT conversion program 530. The CT-to-MR conversion program 520 includes a trained generator 522 that has been trained CT-to-MR domain conversion. The trained generator 522 is a trained model corresponding to the generator 20G in FIG. 5 or the first generator 220G in FIG. 12. The trained generator 522 is an example of a "first trained model" according to the embodiment of the present disclosure. The CT image input to the first generator 220G is an example of a "first medical image" according to the embodiment of the present disclosure. The pseudo 1\4R image output from the first generator 220G is an example of a "second medical image" according to the embodiment of the present disclosure. The pseudo 1\4R image output from the trained generator 522 is an example of the "second medical image" according to the embodiment of the present disclosure.

The MR-to-CT conversion program 530 includes a trained generator 532 that has been trained MR-to-CT domain conversion. The trained generator 532 is a trained model corresponding to the second generator 250F in FIG. 12.

The computer-readable medium 504 may further include at least one program of an organ recognition AI program 540, a disease detection AI program 542, or a report creation support program 544.

The organ recognition AI program 540 includes a processing module that performs organ segmentation. The organ recognition AI program 540 may include a lung section labeling program, a blood vessel region extraction program, a bone labeling program, and the like. The disease detection AI program 542 includes a detection processing module corresponding to a specific disease. As the disease detection AI program 542, for example, at least one program of a lung nodule detection program, a lung nodule characteristic analysis program, a pneumonia CAD program, a mammary gland CAD program, a liver CAD program, a brain CAD program, or a colon CAD program may be included.

The report creation support program 544 includes a trained document generation model that generates a medical opinion candidate corresponding to a target medical image.

Various processing programs such as the organ recognition AI program 540, the disease detection AI program 542, and the report creation support program 544 may be AI processing modules including a trained model that is trained to obtain an output of a target task by applying machine learning such as deep learning.

An AI model for CAD can be configured using, for example, various CNNs having a convolutional layer. Input data for the AI model may include, for example, a medical image such as a two-dimensional image, a three-dimensional image, or a motion picture image, and an output from the AI model may be, for example, information indicating a position of a disease region (lesion portion) in the image, information indicating a class classification such as a disease name, or a combination thereof.

An AI model that handles time series data, document data, and the like can be configured, for example, using various recurrent neural networks (RNNs). In the time series data, for example, waveform data of an electrocardiogram is included. In the document data, for example, a medical opinion created by a doctor is included.

The generated image generated by the CT-to-MR conversion program 520 or the MR-to-CT conversion program 530 can be input to at least one program of the organ recognition AI program 540, the disease detection AI program 542, or the report creation support program 544. Accordingly, an AI processing module constructed by a specific modality can be also applied to an image of another modality, thereby expanding the application range.

Modification Example 3

While the CycleGAN-based training framework is adopted in the second embodiment, the present disclosure is not limited thereto, and for example, it is possible to change an input to a discriminator based on StarGAN performing multi-modality conversion, multimodal unsupervised image-to-image translation (MUNIT), or the like, and to introduce coordinate information obtained from a human body coordinate system into training. As a document describing the StarGAN, there is "Yunjey Choi, Minje Choi, Munyoung Kim, Jung-Woo Ha, Sunghun Kim, Jaegul Choo, "StarGAN: Unified Generative Adversarial Networks for Multi-Domain Image-to-Image Translation" arxiv: 1711.09020". As a document describing the MUNIT, there is "Xun Huang, Ming-Yu Liu, Serge Belongie, Jan Kautz, "Multimodal Unsupervised Image-to-Image Translation" arxiv: 1804.04732".

Modification Example 4

The technology of the present disclosure can target various types of image data. The CT images may include contrast-enhanced CT images captured using a contrast agent and non-enhanced CT images captured without using the contrast agent. In addition, the MR image may include a T1 weighted image, an EOB contrast image, a non-contrast image, an in-phase image, an out-of-phase image, a T2 weighted image, a fat-suppressed image, and the like. EOB is an MRI contrast agent containing gadoxetate sodium (Gd-EOB-DTPA).

Although an example of an image generation task between heterogeneous modalities of CT and MR has been described as an example of domain conversion, the technology of the present disclosure can be applied not only to CT-to-MR as a method of selecting two domains, but also to a conversion task to different imaging parameters such as T1-weighted-T2-weighted in MR, or conversion between a contrast image and a non-contrast image in CT, or the like as another example of domain conversion.

<<About Type of Three-Dimensional Image>>

The technology of the present disclosure is not limited to the CT image and the MR image, and can target various medical images, which are captured by various medical apparatus, such as an ultrasound image for projecting human body information and a positron emission tomography (PET) image captured using a PET apparatus.

Example of Hardware Configuration of Computer

Figure 15:
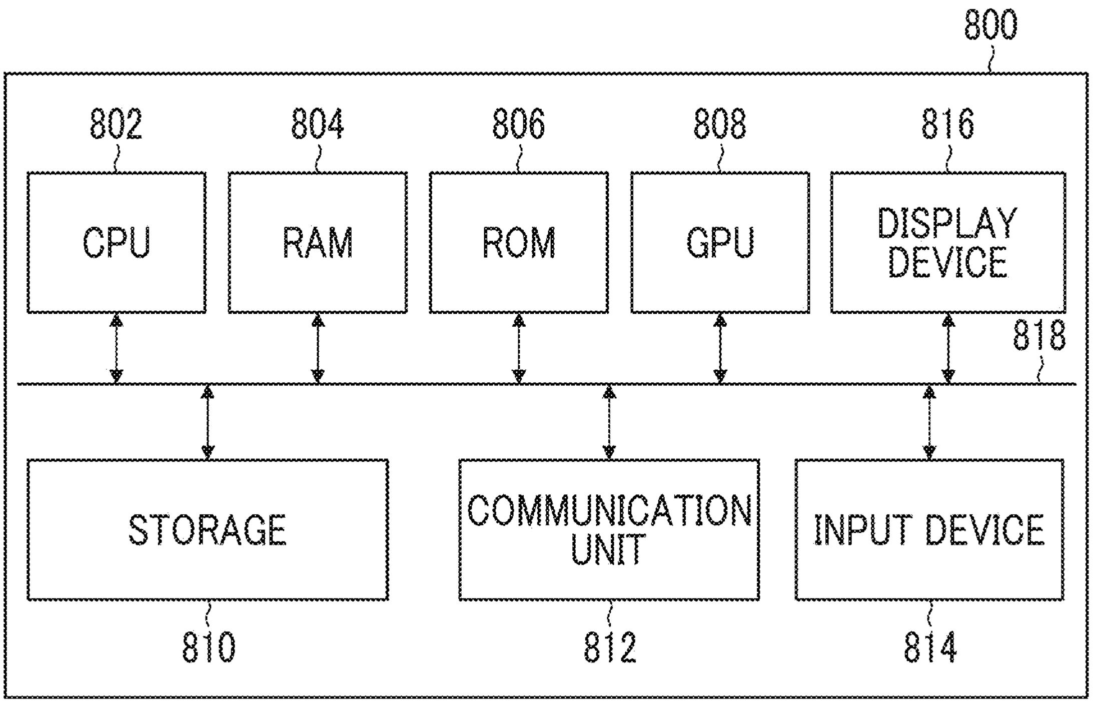
FIG. 15 is a block diagram illustrating an example of a hardware configuration of a computer.

FIG. 15 is a block diagram illustrating an example of a hardware configuration of the computer. A computer 800 may be a personal computer, a workstation, or a server computer. The computer 800 can be used as an apparatus that comprises a part or all of any of the machine learning systems 10 and 210 and the medical image processing apparatus 500 described above, or that has a plurality of functions thereof.

The computer 800 comprises a CPU 802, a random access memory (RAM) 804, a read only memory (ROM) 806, a GPU 808, a storage 810, a communication unit 812, an input device 814, a display device 816, and a bus 818. The GPU 808 may be provided as needed.

The CPU 802 reads out various programs stored in the ROM 806, the storage 810, or the like and performs various types of processing. The RAM 804 is used as a work region of the CPU 802. In addition, the RAM 804 is used as a storage unit that transitorily stores the read-out programs and various types of data.

For example, the storage 810 is configured to include a hard disk apparatus, an optical disc, a magneto-optical disk, a semiconductor memory, or a storage device configured using an appropriate combination thereof. The storage 810 stores various programs, data, and the like. By loading the programs stored in the storage 810 into the RAM 804 and performing the programs via the CPU 802, the computer 800 functions as a unit that performs various types of processing defined by the programs.

The communication unit 812 is an interface for performing communication processing with an external apparatus in a wired or wireless manner and exchanging information with the external apparatus. The communication unit 812 can have a role as an information acquisition unit that receives an input of the image and the like.

The input device 814 is an input interface for receiving various operation inputs for the computer 800. For example, the input device 814 may be a keyboard, a mouse, a multi-touch panel, other pointing devices, a voice input device, or an appropriate combination thereof.

The display device 816 is an output interface on which various types of information are displayed. For example, the display device 816 may be a liquid crystal display, an organic electro-luminescence (OEL) display, a projector, or an appropriate combination thereof <<About Program for Operating Computer>>

A program that causes the computer to implement a part or all of at least one processing function of various processing functions such as a data acquisition function, a preprocessing function, and training processing function in the machine learning systems 10 and 210, and an image processing function in the medical image processing apparatus 500 described in the above-described embodiment can be recorded on a computer-readable medium that is an optical disc, a magnetic disk, a semiconductor memory, or another non-transitory tangible information storage medium, and the program can be provided via the information storage medium.

In addition, instead of an aspect of providing the program by storing the program in the non-transitory tangible computer-readable medium, a program signal can be provided as a download service by using an electric communication line such as the Internet.

Further, at least one processing function among various processing functions such as the data acquisition function, the preprocessing function, and the training processing function in the machine learning systems 10 and 210, and the image processing function in the medical image processing apparatus 500 may be implemented by cloud computing or may be provided as a software as a service (SaaS) service.

<<About Hardware Configuration of Each Processing Unit>>

The hardware structures of processing units performing various processing, such as the generator 20G, the coordinate information combining unit 22, the discriminator 24D, the training data generation unit 30, the coordinate information generation unit 33, the crop processing unit 34, the data acquisition unit 42, the training processing units 40 and 240, the error calculation units 46 and 246, the optimizers 48 and 248, the preprocessing unit 230, the first generator 220G, the second generator 250F, the coordinate information combining units 222 and 256, the first discriminator 224D, and the second discriminator 266D, are, for example, various processors described below.

The various processors include a CPU that is a general-purpose processor functioning as various processing units by executing a program, a GPU that is a processor specialized in image processing, a programmable logic device (PLD) such as a field programmable gate array (FPGA) that is a processor of which a circuit configuration can be changed after manufacture, a dedicated electric circuit such as an application specific integrated circuit (ASIC) that is a processor having a circuit configuration dedicatedly designed to execute specific processing, and the like.

One processing unit may be composed of one of the various processors or may be composed of two or more processors of the same type or heterogeneous types. For example, one processing unit may be composed of a plurality of FPGAs, a combination of a CPU and an FPGA, or a combination of a CPU and a GPU. In addition, a plurality of processing units may be composed of one processor. Examples of the plurality of processing units composed of one processor include, first, as represented by a computer such as a client or a server, a form in which one processor is composed of a combination of one or more CPUs and software, and this processor functions as the plurality of processing units. Second, as represented by a system on chip (SoC) or the like, a form of using a processor that implements functions of the whole system including the plurality of processing units via one integrated circuit (IC) chip is included. Accordingly, various processing units are configured using one or more of the various processors as a hardware structure.

Further, the hardware structure of the various processors is more specifically an electric circuit (circuitry) in which circuit elements such as semiconductor elements are combined.

Other

Configurations of the embodiment of the present invention described above can be appropriately changed, added, or removed without departing from the gist of the present invention. The present invention is not limited to the embodiment described above and can be subjected to many modifications by those having ordinary knowledge in the field within the technical idea of the present invention.

EXPLANATION OF REFERENCES

10: machine learning system
20G generator
22: coordinate information combining unit
24D: discriminator
30 training data generation unit
33: coordinate information generation unit
34: crop processing unit
40 training processing unit
42: data acquisition unit
44: learning model
46: error calculation unit
48: optimizer

50 image storage unit
54: training data storage unit
210: machine learning system
220G: first generator
222: coordinate information combining unit
224D: first discriminator
230: preprocessing unit
240: training processing unit
244: learning model
246: error calculation unit
248: optimizer
250F: second generator
256: coordinate information combining unit
266D: second discriminator
400: information processing apparatus
402: processor
404: computer-readable medium
406: communication interface
408: input-output interface
410: bus
414: input device
416: display device
420: training data generation program
422: coordinate information generation program
424: crop processing program
430: training processing program
436: error calculation program
438: parameter update program
500: medical image processing apparatus
502: processor
504: computer-readable medium
506: communication interface
508: input-output interface
510: bus
514: input device
516: display device
520: CT-to-MR conversion program
522: trained generator
530: MR-to-CT conversion program
532: trained generator
540: organ recognition AI program
542: disease detection AI program
544: report creation support program
800: computer
802: CPU
804: RAM
806: ROM
808: GPU
810: storage
812: communication unit
814: input device
816: display device
818: bus
CTr: CT image
MRr: MR image
MRsyn: pseudo MR image
CTsynrec: reconstructed pseudo CT image
CTsyn: pseudo CT image
MRsynrec: reconstructed pseudo MR image

What is claimed is:

1. A method of generating a trained model that converts a domain of a medical image which is input, and outputs a generated image of a different domain, wherein a learning model is used, which has a structure of a generative adversarial network including a first generator configured using a first convolutional neural network that receives an input of a medical image of a first domain corresponding to a first medical imaging apparatus and that outputs a pseudo image of a second domain different from the first domain, corresponding to a second medical imaging apparatus different from the first medical imaging apparatus, and a first discriminator configured using a second convolutional neural network that receives an input of data including first image data and coordinate information of a human body coordinate system corresponding to each position of a plurality of unit elements configuring the first image data, and that discriminates whether an input image related to the second domain is a real image imaged by the second imaging apparatus or a fake image generated by the first generator, wherein the first image data is the pseudo image of the second domain or an actual medical image of the second domain included in a training dataset, and the method comprises:

by a computer, acquiring a plurality of pieces of training data including a first medical image imaged by the first medical imaging apparatus and a second medical image imaged by the second medical imaging apparatus having a same imaging region; and performing training processing of training the first generator and the first discriminator in an adversarial manner based on the plurality of pieces of training data.

2. The method of generating a trained model according to claim 1, wherein the coordinate information corresponding to the pseudo image of the second domain in a case where the pseudo image of the second domain is input to the first discriminator is coordinate information determined for the medical image of the first domain which is a conversion source image input to the first generator in a case of generating the pseudo image of the second domain.

3. The method of generating a trained model according to claim 1, wherein the first image data is three-dimensional data, the coordinate information includes x coordinate information, y coordinate information, and z coordinate information that specify a position of each voxel as the unit element in a three-dimensional space, and the x coordinate information, the y coordinate information, and the z coordinate information are used as channels and are combined with a channel of the first image data or a feature map of the first image data to be given to the first discriminator.

4. The method of generating a trained model according to claim 1, wherein the coordinate information of the human body coordinate system is an absolute coordinate defined with reference to an anatomical position of a portion of a human body, and for each medical image used as the training data, the coordinate information corresponding to each unit element in the image is associated.

5. The method of generating a trained model according to claim 4, further comprising:

by the computer, generating, for each medical image used as the training data, the coordinate information corresponding to each unit element in the image.

6. The method of generating a trained model according to claim 1, wherein the coordinate information is input in an inter-layer of the second convolutional neural network.

7. The method of generating a trained model according to claim 1, wherein the learning model further includes a second generator configured using a third convolutional neural network that receives an input of the medical image of the second domain and that outputs a pseudo image of the first domain, and a second discriminator configured using a fourth convolutional neural network that receives an input of data including second image data and coordinate information of the human body coordinate system corresponding to each position of a plurality of unit elements configuring the second image data, and that discriminates whether an input image related to the first domain is a real image imaged by the first imaging apparatus or a fake image generated by the second generator, wherein the second image data is the pseudo image of the first domain or an actual medical image of the first domain included in the training dataset, and the training processing includes processing of training the second generator and the second discriminator in an adversarial manner.

8. The method of generating a trained model according to claim 7, wherein the coordinate information corresponding to the second generated image in a case where the pseudo image of the first domain is input to the second discriminator is coordinate information determined for the medical image of the second domain which is a conversion source image input to the second generator in a case of generating the second generated image.

9. The method of generating a trained model according to claim 7, further comprising:

by the computer, performing processing of calculating a first reconstruction loss of conversion processing using the first generator and the second generator in this order based on a first reconstructed image output from the second generator by inputting the pseudo image of the second domain output from the first generator to the second generator; and processing of calculating a second reconstruction loss of conversion processing using the second generator and the first generator in this order based on a second reconstructed image output from the first generator by inputting the pseudo image of the first domain output from the second generator to the first generator.

10. The method of generating a trained model according to claim 1, wherein the medical image of the first domain is a first modality image captured using the first medical imaging apparatus, the medical image of the second domain is a second modality image captured using the second imaging apparatus, and the learning model receives an input of the first modality image and is trained to generate a pseudo second modality generated image having a feature of the image captured using the second modality.

11. A machine learning system for training a learning model that converts a domain of a medical image which is input, and generates a generated image of a different domain, the system comprising:

at least one first processor; and at least one first storage device in which a program executed by the at least one first processor is stored, wherein the learning model having a structure of a generative adversarial network including a first generator configured using a first convolutional neural network that receives an input of a medical image of a first domain corresponding to a first medical imaging apparatus and that outputs a pseudo image of a second domain different from the first domain, corresponding to a second medical imaging apparatus different from the first medical imaging apparatus, and a first discriminator configured using a second convolutional neural network that receives an input of data including first image data and coordinate information of a human body coordinate system corresponding to each position of a plurality of unit elements configuring the first image data, and that discriminates whether an input image related to the second domain is a real image imaged by the second imaging apparatus or a fake image generated by the first generator, wherein the first image data is the pseudo image of the second domain or an actual medical image of the second domain included in a training dataset, and the at least one first processor, by executing an instruction of the program, acquires a plurality of pieces of training data including a first medical image imaged by the first medical imaging apparatus and a second medical image imaged by the second medical imaging apparatus having a same imaging region, and performs training processing of training the first generator and the first discriminator in an adversarial manner based on the plurality of pieces of training data.

12. A non-transitory, computer-readable tangible recording medium on which a program for causing, when read by a computer, the computer to execute the method of generating a trained model according to claim 1 is recorded.

13. A medical image processing apparatus comprising:

a second storage device that stores a first trained model which is the trained first generator trained by implementing the method of generating a trained model according to claim 1; and a second processor that performs image processing using the first trained model, wherein the first trained model is a model that receives an input of a first medical image and is trained to output a second medical image of a domain different from the first medical image.

* * * * *